(12) United States Patent
Markowitz et al.

(10) Patent No.: US 8,494,614 B2
(45) Date of Patent: Jul. 23, 2013

(54) COMBINATION LOCALIZATION SYSTEM

(75) Inventors: H. Toby Markowitz, Roseville, MN (US); Kenneth Gardeski, Plymouth, MN (US); Jean Carver, Blaine, MN (US); Kendra Yasger, Big Lake, MN (US); Michael R. Neidert, Salthill (IE); Lane A. Phillips, Minneapolis, MN (US); Laurent Verard, Andover, MA (US); Steven L. Hartmann, Superior, CO (US); Andrew Bzostek, Erie, CO (US); Bradley A. Jascob, Broomfield, CO (US)

(73) Assignees: Regents of the University of Minnesota, St. Paul, MN (US); Medtronic, Inc., Minneapolis, MN (US)

( * ) Notice: Subject to any disclaimer, the term of this patent is extended or adjusted under 35 U.S.C. 154(b) by 222 days.

(21) Appl. No.: 12/844,065

(22) Filed: Jul. 27, 2010

(65) Prior Publication Data

US 2011/0054293 A1 Mar. 3, 2011

Related U.S. Application Data

(60) Provisional application No. 61/238,623, filed on Aug. 31, 2009.

(51) Int. Cl.
*A61B 5/05* (2006.01)
(52) U.S. Cl.
USPC ........................................... 600/424; 600/407
(58) Field of Classification Search
USPC ............ 600/407, 424, 427; 128/899; 607/122
See application file for complete search history.

(56) References Cited

U.S. PATENT DOCUMENTS

| | | | |
|---|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |

(Continued)

FOREIGN PATENT DOCUMENTS

| CA | 964149 A1 | 3/1975 |
| CN | 101711125 A | 5/2010 |

(Continued)

OTHER PUBLICATIONS

Birkfellner, Wolfgang, et al. "Calibration of Tracking Systems in a Surgical Environment," IEEE Transactions on Medical Imaginge, IEEE Service Center, Piscataway, NJ, US, vol. 17, No. 5. (Oct. 1, 1998) XP011035767. ISSN: 0278-0062 the whole document.

(Continued)

*Primary Examiner* — Michael Rozanski
(74) *Attorney, Agent, or Firm* — Harness, Dickey

(57) ABSTRACT

A navigation system or combination of navigation systems can be used to provide two or more navigation modalities to navigate a single instrument in a volume. For example, both an Electromagnetic (EM) and Electropotential (EP) navigation system can be used to navigate an instrument within the volume. Image data can also be illustrated relative to a tracked position of the instrument in the volume for navigation.

39 Claims, 12 Drawing Sheets

U.S. PATENT DOCUMENTS

| | | |
|---|---|---|
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,837,347 A | 9/1974 | Tower |
| 3,868,565 A | 2/1975 | Kuipers |
| 3,941,127 A | 3/1976 | Froning |
| 3,983,474 A | 9/1976 | Kuipers |
| 3,995,623 A | 12/1976 | Blake et al. |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,506,680 A | 3/1985 | Stokes |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,619,246 A | 10/1986 | Molgaard-Nielsen et al. |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,649,924 A | 3/1987 | Taccardi |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,696,304 A | 9/1987 | Chin |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,801,297 A | 1/1989 | Mueller |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,852,580 A | 8/1989 | Wood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,035,246 A | 7/1991 | Heuvelmans et al. |
| 5,042,486 A | 8/1991 | Pfeiler et al. |
| 5,047,036 A | 9/1991 | Koutrouvelis |
| 5,050,608 A | 9/1991 | Watanabe et al. |

| Patent No. | Date | Inventor |
|---|---|---|
| 5,054,492 A | 10/1991 | Scribner et al. |
| 5,057,095 A | 10/1991 | Fabian |
| 5,059,789 A | 10/1991 | Salcudean |
| 5,076,285 A | 12/1991 | Hess et al. |
| 5,078,140 A | 1/1992 | Kwoh |
| 5,078,714 A | 1/1992 | Katims |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,167,239 A | 12/1992 | Cohen et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,265,622 A | 11/1993 | Barbere |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,342,295 A | 8/1994 | Imran |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,512,920 A | 4/1996 | Gibson |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,522,874 A | 6/1996 | Gates |

| Patent No. | Date | Inventor |
|---|---|---|
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,639,276 A | 6/1997 | Weinstock et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,407 A | 9/1998 | Eldor |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,916,193 A | 6/1999 | Stevens et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,944,022 A | 8/1999 | Nardella et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,964,796 A | 10/1999 | Imran |
| 5,967,980 A | 10/1999 | Ferre et al. |
| 5,967,982 A | 10/1999 | Barnett |

| | | |
|---|---|---|
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,009,349 A | 12/1999 | Mouchawar et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,267 A | 4/2000 | Nardella et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,088,527 A | 7/2000 | Rybczynski |
| 6,090,105 A | 7/2000 | Zepeda et al. |
| 6,096,050 A | 8/2000 | Audette |
| 6,104,944 A | 8/2000 | Martinelli |
| 6,112,111 A | 8/2000 | Glantz |
| 6,118,845 A | 9/2000 | Simon et al. |
| 6,122,538 A | 9/2000 | Sliwa, Jr. et al. |
| 6,122,541 A | 9/2000 | Cosman et al. |
| 6,122,552 A | 9/2000 | Tockman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,152,946 A | 11/2000 | Broome et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,192,280 B1 | 2/2001 | Sommer et al. |
| 6,194,639 B1 | 2/2001 | Botella et al. |
| 6,196,230 B1 | 3/2001 | Hall et al. |
| 6,201,387 B1 | 3/2001 | Govari |
| 6,203,493 B1 | 3/2001 | Ben-Haim |
| 6,203,497 B1 | 3/2001 | Dekel et al. |
| 6,207,111 B1 | 3/2001 | Weinberg |
| 6,210,362 B1 | 4/2001 | Ponzi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,226,547 B1 | 5/2001 | Lockhart et al. |
| 6,233,476 B1 | 5/2001 | Strommer et al. |
| 6,236,875 B1 | 5/2001 | Bucholz et al. |
| 6,236,886 B1 | 5/2001 | Cherepenin et al. |
| 6,240,307 B1 | 5/2001 | Beatty et al. |
| 6,246,231 B1 | 6/2001 | Ashe |
| 6,246,468 B1 | 6/2001 | Dimsdale |
| 6,253,770 B1 | 7/2001 | Acker et al. |
| 6,256,121 B1 | 7/2001 | Lizotte et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,301,498 B1 | 10/2001 | Greenberg et al. |
| 6,314,310 B1 | 11/2001 | Ben-Haim et al. |
| 6,330,356 B1 | 12/2001 | Sundareswaran et al. |
| 6,332,089 B1 | 12/2001 | Acker et al. |
| 6,341,231 B1 | 1/2002 | Ferre et al. |
| 6,351,659 B1 | 2/2002 | Vilsmeier |
| 6,379,302 B1 | 4/2002 | Kessman et al. |
| 6,381,485 B1 | 4/2002 | Hunter et al. |
| 6,389,187 B1 | 5/2002 | Greenaway et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,447,504 B1 | 9/2002 | Ben-Haim et al. |
| 6,470,205 B2 | 10/2002 | Bosselmann et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,474 B1 | 12/2002 | Willis et al. |
| 6,490,475 B1 | 12/2002 | Seeley et al. |
| 6,493,573 B1 | 12/2002 | Martinelli et al. |
| 6,493,575 B1 | 12/2002 | Kesten et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,527,782 B2 | 3/2003 | Hogg et al. |
| 6,546,270 B1 | 4/2003 | Goldin et al. |
| 6,551,325 B2 | 4/2003 | Neubauer et al. |
| 6,569,160 B1 | 5/2003 | Goldin et al. |
| 6,574,498 B1 | 6/2003 | Gilboa |
| 6,584,174 B2 | 6/2003 | Schubert et al. |
| 6,593,884 B1 | 7/2003 | Gilboa et al. |
| 6,595,989 B1 | 7/2003 | Schaer |
| 6,602,271 B2 | 8/2003 | Adams et al. |
| 6,609,022 B2 | 8/2003 | Vilsmeier et al. |
| 6,611,141 B1 | 8/2003 | Schulz et al. |
| 6,611,700 B1 | 8/2003 | Vilsmeier et al. |
| 6,640,128 B2 | 10/2003 | Vilsmeier et al. |
| 6,694,162 B2 | 2/2004 | Hartlep |
| 6,701,176 B1 | 3/2004 | Halperin et al. |
| 6,701,179 B1 | 3/2004 | Martinelli et al. |
| 6,711,429 B1 | 3/2004 | Gilboa et al. |
| 6,714,806 B2 | 3/2004 | Iaizzo et al. |
| 6,725,080 B2 | 4/2004 | Melkent et al. |
| 6,771,996 B2 | 8/2004 | Bowe et al. |
| 6,868,195 B2 | 3/2005 | Fujita |
| 6,888,623 B2 | 5/2005 | Clements |
| 6,892,090 B2 | 5/2005 | Verard et al. |
| 6,892,091 B1 | 5/2005 | Ben-Haim et al. |
| 6,898,302 B1 | 5/2005 | Brummer |
| 6,950,689 B1 | 9/2005 | Willis et al. |
| 6,990,370 B1 | 1/2006 | Beatty et al. |
| 7,020,522 B1 | 3/2006 | Hoijer et al. |
| 7,047,073 B2 | 5/2006 | Hoijer et al. |
| 7,130,700 B2 | 10/2006 | Gardeski et al. |
| 7,189,208 B1 | 3/2007 | Beatty et al. |
| 7,207,989 B2 | 4/2007 | Pike, Jr. et al. |
| 7,215,430 B2 | 5/2007 | Kacyra et al. |
| 7,263,397 B2 | 8/2007 | Hauck et al. |
| 7,305,121 B2 | 12/2007 | Kaufmann et al. |
| 7,328,071 B1 | 2/2008 | Stehr et al. |
| 7,369,901 B1 | 5/2008 | Morgan et al. |
| 7,421,300 B2 | 9/2008 | Smits |
| 7,479,141 B2 | 1/2009 | Kleen et al. |
| 7,529,584 B2 | 5/2009 | Laske et al. |
| 7,570,791 B2 | 8/2009 | Frank et al. |
| 7,599,730 B2 | 10/2009 | Hunter et al. |
| 7,686,757 B2 | 3/2010 | Minai |
| 7,697,972 B2 | 4/2010 | Verard et al. |
| 7,715,604 B2 | 5/2010 | Sun et al. |
| 7,824,328 B2 | 11/2010 | Gattani et al. |
| 7,848,787 B2 | 12/2010 | Osadchy |
| 7,941,213 B2 | 5/2011 | Markowitz et al. |
| 7,988,639 B2 | 8/2011 | Starks |
| 8,046,052 B2 | 10/2011 | Verard et al. |
| 8,060,185 B2 | 11/2011 | Hunter et al. |
| 8,106,905 B2 | 1/2012 | Markowitz et al. |
| 8,135,467 B2 | 3/2012 | Markowitz et al. |
| 8,175,681 B2 | 5/2012 | Hartmann et al. |

| | | |
|---|---|---|
| 8,185,192 B2 | 5/2012 | Markowitz et al. |
| 8,208,991 B2 | 6/2012 | Markowitz et al. |
| 8,214,018 B2 | 7/2012 | Markowitz et al. |
| 8,260,395 B2 | 9/2012 | Markowitz et al. |
| 2001/0000800 A1 | 5/2001 | Partridge et al. |
| 2001/0007918 A1 | 7/2001 | Vilsmeier et al. |
| 2001/0031920 A1 | 10/2001 | Kaufman et al. |
| 2001/0036245 A1 | 11/2001 | Kienzle et al. |
| 2002/0045810 A1 | 4/2002 | Ben-Haim |
| 2002/0049375 A1 | 4/2002 | Strommer et al. |
| 2002/0077544 A1 | 6/2002 | Shahidi |
| 2002/0077568 A1 | 6/2002 | Haddock |
| 2002/0095081 A1 | 7/2002 | Vilsmeier et al. |
| 2002/0111662 A1 | 8/2002 | Iaizzo et al. |
| 2002/0128565 A1 | 9/2002 | Rudy |
| 2002/0147488 A1 | 10/2002 | Doan et al. |
| 2002/0183817 A1 | 12/2002 | Van Venrooij et al. |
| 2002/0193686 A1 | 12/2002 | Gilboa |
| 2003/0018251 A1 | 1/2003 | Solomon |
| 2003/0028118 A1 | 2/2003 | Dupree et al. |
| 2003/0055324 A1 | 3/2003 | Wasserman |
| 2003/0074011 A1 | 4/2003 | Gilboa et al. |
| 2003/0078494 A1 | 4/2003 | Panescu et al. |
| 2003/0108853 A1 | 6/2003 | Chosack et al. |
| 2003/0114908 A1 | 6/2003 | Flach |
| 2003/0225434 A1 | 12/2003 | Glantz et al. |
| 2003/0231789 A1 | 12/2003 | Willis et al. |
| 2004/0001075 A1 | 1/2004 | Balakrishnan et al. |
| 2004/0019318 A1 | 1/2004 | Wilson et al. |
| 2004/0019359 A1 | 1/2004 | Worley et al. |
| 2004/0024309 A1 | 2/2004 | Ferre et al. |
| 2004/0044295 A1 | 3/2004 | Reinert et al. |
| 2004/0064159 A1 | 4/2004 | Hoijer et al. |
| 2004/0068312 A1 | 4/2004 | Sigg et al. |
| 2004/0070582 A1 | 4/2004 | Smith et al. |
| 2004/0097805 A1 | 5/2004 | Verard et al. |
| 2004/0097806 A1 | 5/2004 | Hunter et al. |
| 2004/0162599 A1 | 8/2004 | Kurth |
| 2004/0215298 A1 | 10/2004 | Richardson et al. |
| 2004/0228453 A1 | 11/2004 | Dobbs et al. |
| 2004/0236395 A1 | 11/2004 | Iaizzo et al. |
| 2004/0249281 A1 | 12/2004 | Olstad |
| 2004/0249430 A1 | 12/2004 | Martinez et al. |
| 2004/0254437 A1 | 12/2004 | Hauck et al. |
| 2005/0004476 A1 | 1/2005 | Payvar et al. |
| 2005/0018888 A1 | 1/2005 | Zonneveld |
| 2005/0119550 A1 | 6/2005 | Serra et al. |
| 2005/0143651 A1 | 6/2005 | Verard et al. |
| 2005/0177151 A1 | 8/2005 | Coen et al. |
| 2005/0187432 A1 | 8/2005 | Hale et al. |
| 2005/0245803 A1 | 11/2005 | Glenn Jr. et al. |
| 2005/0288586 A1 | 12/2005 | Ferek-Petric |
| 2006/0013523 A1 | 1/2006 | Childlers et al. |
| 2006/0058604 A1 | 3/2006 | Avinash et al. |
| 2006/0116576 A1 | 6/2006 | McGee et al. |
| 2006/0117773 A1 | 6/2006 | Street et al. |
| 2006/0135883 A1 | 6/2006 | Jonsson et al. |
| 2006/0153468 A1 | 7/2006 | Solf et al. |
| 2006/0173268 A1 | 8/2006 | Mullick et al. |
| 2006/0173381 A1 | 8/2006 | Eck |
| 2006/0200049 A1 | 9/2006 | Leo et al. |
| 2006/0206157 A1 | 9/2006 | Hoijer |
| 2006/0229513 A1 | 10/2006 | Wakai |
| 2006/0229594 A1 | 10/2006 | Francischelli et al. |
| 2006/0247520 A1 | 11/2006 | McGee |
| 2006/0253116 A1 | 11/2006 | Avitall et al. |
| 2007/0016084 A1 | 1/2007 | Denault |
| 2007/0038052 A1 | 2/2007 | Swoyer et al. |
| 2007/0043413 A1 | 2/2007 | Eversull et al. |
| 2007/0046661 A1 | 3/2007 | Ma et al. |
| 2007/0049817 A1 | 3/2007 | Preiss et al. |
| 2007/0066889 A1 | 3/2007 | Boese et al. |
| 2007/0112388 A1 | 5/2007 | Salo |
| 2007/0123944 A1 | 5/2007 | Zdeblick |
| 2007/0135721 A1 | 6/2007 | Zdeblick |
| 2007/0135803 A1 | 6/2007 | Belson |
| 2007/0156019 A1 | 7/2007 | Larkin et al. |
| 2007/0164900 A1 | 7/2007 | Schneider et al. |
| 2007/0167801 A1 | 7/2007 | Webler et al. |
| 2007/0232898 A1 | 10/2007 | Huynh et al. |
| 2007/0252074 A1 | 11/2007 | Ng et al. |
| 2007/0270682 A1 | 11/2007 | Huang et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0015466 A1 | 1/2008 | Lerman |
| 2008/0024493 A1 | 1/2008 | Bordoloi et al. |
| 2008/0038197 A1 | 2/2008 | John et al. |
| 2008/0058656 A1 | 3/2008 | Costello et al. |
| 2008/0071142 A1 | 3/2008 | Gattani et al. |
| 2008/0118117 A1 | 5/2008 | Gauldie et al. |
| 2008/0123910 A1 | 5/2008 | Zhu |
| 2008/0132800 A1 | 6/2008 | Hettrick et al. |
| 2008/0183072 A1 | 7/2008 | Robertson et al. |
| 2008/0207997 A1 | 8/2008 | Higgins et al. |
| 2008/0221425 A1 | 9/2008 | Olson et al. |
| 2008/0221438 A1 | 9/2008 | Chen et al. |
| 2008/0243025 A1 | 10/2008 | Holmstrom et al. |
| 2008/0249375 A1 | 10/2008 | Obel |
| 2008/0255470 A1 | 10/2008 | Hauck et al. |
| 2008/0319297 A1 | 12/2008 | Danehorn |
| 2009/0017430 A1 | 1/2009 | Muller-Daniels et al. |
| 2009/0063118 A1 | 3/2009 | Dachille et al. |
| 2009/0093857 A1 | 4/2009 | Markowitz et al. |
| 2009/0099619 A1 | 4/2009 | Lessmeier et al. |
| 2009/0103793 A1 | 4/2009 | Borland et al. |
| 2009/0126575 A1 | 5/2009 | Son et al. |
| 2009/0129477 A1 | 5/2009 | Yang |
| 2009/0131955 A1 | 5/2009 | Wenderow et al. |
| 2009/0192381 A1 | 7/2009 | Brockway et al. |
| 2009/0211909 A1 | 8/2009 | Nesbitt |
| 2009/0227861 A1 | 9/2009 | Ganatra et al. |
| 2009/0253976 A1 | 10/2009 | Harlev et al. |
| 2009/0253985 A1 | 10/2009 | Shachar et al. |
| 2009/0262109 A1 | 10/2009 | Markowitz et al. |
| 2009/0262979 A1 | 10/2009 | Markowitz et al. |
| 2009/0262980 A1 | 10/2009 | Markowitz et al. |
| 2009/0262982 A1 | 10/2009 | Markowitz et al. |
| 2009/0262992 A1 | 10/2009 | Markowitz et al. |
| 2009/0264727 A1 | 10/2009 | Markowitz et al. |
| 2009/0264738 A1 | 10/2009 | Markowitz et al. |
| 2009/0264739 A1 | 10/2009 | Markowitz et al. |
| 2009/0264740 A1 | 10/2009 | Markowitz et al. |
| 2009/0264741 A1 | 10/2009 | Markowitz et al. |
| 2009/0264742 A1 | 10/2009 | Markowitz et al. |
| 2009/0264743 A1 | 10/2009 | Markowitz et al. |
| 2009/0264744 A1 | 10/2009 | Markowitz et al. |
| 2009/0264745 A1 | 10/2009 | Markowitz et al. |
| 2009/0264746 A1 | 10/2009 | Markowitz et al. |
| 2009/0264747 A1 | 10/2009 | Markowitz et al. |
| 2009/0264748 A1 | 10/2009 | Markowitz et al. |
| 2009/0264749 A1 | 10/2009 | Markowitz et al. |
| 2009/0264750 A1 | 10/2009 | Markowitz et al. |
| 2009/0264751 A1 | 10/2009 | Markowitz et al. |
| 2009/0264752 A1 | 10/2009 | Markowitz et al. |
| 2009/0264777 A1 | 10/2009 | Markowitz et al. |
| 2009/0264778 A1 | 10/2009 | Markowitz et al. |
| 2009/0265128 A1 | 10/2009 | Markowitz et al. |
| 2009/0267773 A1 | 10/2009 | Markowitz et al. |
| 2009/0281417 A1 | 11/2009 | Hartmann et al. |
| 2009/0297001 A1 | 12/2009 | Markowitz et al. |
| 2009/0306732 A1 | 12/2009 | Rosenberg et al. |
| 2010/0004724 A1 | 1/2010 | Markowitz et al. |
| 2010/0022873 A1 | 1/2010 | Hunter et al. |
| 2010/0030061 A1 | 2/2010 | Canfield et al. |
| 2010/0030063 A1 | 2/2010 | Lee et al. |
| 2010/0030298 A1 | 2/2010 | Martens et al. |
| 2010/0152571 A1 | 6/2010 | Hartmann et al. |
| 2010/0210938 A1 | 8/2010 | Verard et al. |
| 2011/0054304 A1 | 3/2011 | Markowitz et al. |
| 2011/0106203 A1 | 5/2011 | Markowitz et al. |
| 2012/0059249 A1 | 3/2012 | Verard et al. |
| 2012/0065481 A1 | 3/2012 | Hunter et al. |
| 2012/0130232 A1 | 5/2012 | Markowitz et al. |
| 2012/0190993 A1 | 7/2012 | Markowitz et al. |
| 2012/0220860 A1* | 8/2012 | Hartmann et al. ............ 600/424 |
| 2012/0226110 A1 | 9/2012 | Markowitz et al. |

FOREIGN PATENT DOCUMENTS

| | | |
|---|---|---|
| CN | 102056537 A | 5/2011 |
| CN | 102118994 A | 7/2011 |
| DE | 3042343 A1 | 6/1982 |
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 | 11/2002 |
| EP | 0062941 | 10/1982 |
| EP | 0119660 A1 | 9/1984 |
| EP | 0155857 | 9/1985 |
| EP | 0319844 | 6/1989 |
| EP | 0326768 A2 | 8/1989 |
| EP | 0350996 A1 | 1/1990 |
| EP | 363117 A1 | 4/1990 |
| EP | 0419729 A1 | 4/1991 |
| EP | 0427358 | 5/1991 |
| EP | 0456103 | 11/1991 |
| EP | 0581704 A1 | 2/1994 |
| EP | 0651968 A1 | 5/1995 |
| EP | 0655138 A1 | 5/1995 |
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 1393674 A1 | 3/2004 |
| EP | 1421913 A1 | 5/2004 |
| EP | 2136706 | 12/2009 |
| EP | 2271253 A1 | 1/2011 |
| EP | 2276402 A1 | 1/2011 |
| EP | 2376935 A1 | 10/2011 |
| EP | 2416832 A1 | 2/2012 |
| EP | 2473130 A2 | 7/2012 |
| FR | 2417970 A1 | 9/1979 |
| FR | 2618211 | 1/1989 |
| GB | 2094590 A | 9/1982 |
| GB | 2164856 A | 4/1986 |
| JP | 62327 | 6/1983 |
| JP | 63240851 A | 10/1988 |
| JP | 2765738 T | 4/1991 |
| JP | 3267054 | 11/1991 |
| JP | 6194639 | 7/1994 |
| WO | WO-8809151 A1 | 12/1988 |
| WO | WO-8905123 | 6/1989 |
| WO | WO-9005494 A1 | 5/1990 |
| WO | WO-9103982 A1 | 4/1991 |
| WO | WO-9104711 A1 | 4/1991 |
| WO | WO-9107726 A1 | 5/1991 |
| WO | WO-9203090 A1 | 3/1992 |
| WO | WO-9206645 A1 | 4/1992 |
| WO | WO-9404938 A1 | 3/1994 |
| WO | WO-9423647 A1 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |
| WO | WO-9838908 A1 | 9/1998 |
| WO | WO-9848722 A1 | 11/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |
| WO | WO-9952094 A1 | 10/1999 |
| WO | WO-9960939 A1 | 12/1999 |
| WO | WO-0006701 A1 | 2/2000 |
| WO | WO-0035531 A1 | 6/2000 |
| WO | WO-0130437 A1 | 5/2001 |
| WO | WO-0134050 A2 | 5/2001 |
| WO | WO-0187136 A2 | 11/2001 |
| WO | WO-02064011 A2 | 8/2002 |
| WO | WO-02064040 A2 | 8/2002 |
| WO | WO-2005112836 A2 | 12/2005 |
| WO | WO-2006042039 A2 | 4/2006 |
| WO | WO-2006117773 A1 | 11/2006 |
| WO | WO-2007067945 | 6/2007 |
| WO | WO-2007111542 A1 | 10/2007 |
| WO | WO-2007136451 A2 | 11/2007 |
| WO | WO-2008108901 | 9/2008 |
| WO | WO-2008147961 A1 | 12/2008 |
| WO | WO-2009086392 A1 | 7/2009 |
| WO | WO-2009126575 A1 | 10/2009 |
| WO | WO-2009129475 A1 | 10/2009 |
| WO | WO-2009129477 A1 | 10/2009 |
| WO | WO-2009129484 A1 | 10/2009 |
| WO | WO-2010074986 A1 | 7/2010 |
| WO | WO-2010118314 A1 | 10/2010 |
| WO | WO-2011025708 A2 | 3/2011 |
| WO | WO-2011026077 A2 | 3/2011 |

OTHER PUBLICATIONS

Hubert-Tremblay, Vincent, et al. "Octree indexing of DICOM images for voxel number reduction and improvement of Monte Carolo simulation computing efficiency," Medical Physics, AIP, Melville, NY, US, vol. 33, No. 8, (Jul. 21, 2006) pp. 2819-2831, XP012092212, ISSN: 0094-2405, DOI: 10.1118/1.2214305 pp. 2820-2821.

International Preliminary Report on Patentability mailed Oct. 11, 2011 for PCT/US2010/030534 darning benefit of U.S. Appl. No. 12/421,375, filed Apr. 9, 2009.

International Search Report and Written Opinon mailed Jul. 25, 2011 for PCT/US2010/047241 claiming benefit of U.S. Appl. No. 12/844,065, filed Jul. 27, 2010.

International Search Report mailed Sep. 13, 2010 for PCT/US2010/030534 claiming benefit of U.S. Appl. No. 12/421,375, filed Apr. 9, 2009.

Invitation to Pay Additional Fees mailed Jul. 7, 2010 for PCT/US2010/030534 claiming benefit of U.S. Appl. No. 12/421,375, filed Apr. 9, 2009.

"EnSite NavX™ Navigation & Visualization Technology." 3 pages, St. Jude Medical. http://www.sjmprofessional.com/Products/US/Mapping-and-Visualization/EnSite-NavXNavigation-and-Visualization-Technology.aspx Web. Accessed Jun. 19, 2009.

"Local Lisa® Intracardiac Navigation System Model 9670000/9670025." Technical Manual Version 1.2, Chapter 1, pp. 1-19. 2004.

"Prestige Cervical Disc System Surgical Technique", 12 pgs.

"Vital Images Receives 510(k) Clearance to Market VScore(TM) With AutoGate(TM); Breakthrough in Cardiac CT Imaging Simplifies Screening for Heart Disease," Press Release. Vital Images, Inc., Feb. 6, 2001 (4 page).

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: A Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Brenner, David J., Ph.D., "Computed Tomography—An Increasing Source of Radiation Exposure", The New England Journal of Medicine (Nov. 29, 2007), pp. 2277-2284.

Brown, R., M.D., A Stereotactic Head Frame for Use with CT Body Scanners, Investigative Radiology .COPYRGT.J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The SteathStation: Three-Dimensional Image-Interactive Guidance for the Spine Surgeon," Spinal Frontiers, Apr. 1996, pp. 7-9.

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. On Biomed. Eng., vol. 89, No. 12, pp. 1226-1231 (1992).

Galloway, R.L., Jr. et al, Optical localization for interactive, image-guided neurosurgery, SPIE, vol. 2164 (May 1, 1994) pp. 137-145.

Gepstein, Lior, M.D., "A Novel Method for Nonfluoroscopic Catheter-Based Electroanatomical Mapping of the Heart, In Vitro and In Vivo Accuracy Results", American Heart Association, Learn and Live, Circulation (1997), http://circ.ahajournals.org/cgi/content/abstract/95/6/1611 printed Oct. 2, 2008.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. 1996, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13 (1994) pp. 193-211.

Hamadeh et al, "Kinematic Study of Lumbar Spine Using Functional Radiographies and 3D/2D Registration," TIMC UMR 5525—IMAG (1997).

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. For Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Homer et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

International Preliminary Report on Patentability and Written Opinion for PCT/US2009/040998 mailed Oct. 28, 2010, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.

International Preliminary Report on Patentability and Written Opinion for PCT/US2009/0400984 mailed Oct. 28, 2010, claiming benefit of U.S. Appl. No. 12/117,549, filed May 8, 2008.

International Preliminary Report on Patentability and Written Opinion for PCT/US2009/040979 mailed Oct. 28, 2010 claiming benefit of U.S. Appl. No. 12/117,537, filed May 8, 2008.

International Preliminary Report on Patentability and Written Opinion mailed Oct. 29, 2009 for PCT/US2007/089087, of which U.S. Appl. No. 12/492,906, filed Jun. 26, 2009 claims benefit.

International Search Report and Written Opinion for PCT/US2008/088189 mailed Apr. 3, 2009, claiming benefit of U.S. Appl. No. 12/183,796, filed Jul. 31, 2008; and claims priority to U.S. Appl. No. 11/966,382, filed Dec. 28, 2007.

International Search Report and Written Opinion for PCT/US2009/0400984 mailed Sep. 21, 2009, claiming benefit of U.S. Appl. No. 12/117,549, filed May 8, 2008.

International Search Report and Written Opinion for PCT/US2009/040998 mailed Jul. 29, 2009 claiming benefit of U.S. Appl. No. 12/421332, filed Apr. 9, 2009; which claims priority to U.S. Appl. No. 61/105,957, filed Oct. 16, 2008; U.S. Appl. No. 12/117,549, filed May 8, 2008.

International Search Report and Written Opinion for PCT/US2009/067486 mailed May 4, 2010, claiming benefit of U.S. Appl. No. 12/336,085, filed Dec. 16, 2008.

International Search Report and Written Opinion mailed Dec. 6, 2010 for PCT/US2010/051248, which claims benefit of U.S. Appl. No. 12/609,734, filed Oct. 30, 2009.

International Search Report and Written Opinion mailed May 4, 2010 for PCT/US2009/067486 claiming benefit of U.S. Appl. No. 12/336,085, filed Dec. 16, 2008.

International Search Report and Written Opinon for PCT/US2009/040979 mailed Sep. 21, 2009 claiming benefit of U.S. Appl. No. 12/117,537, filed May 8, 2008.

International Search Report for PCT/US2007/089087 mailed Jul. 9, 2008, of which U.S. Appl. No. 12/492,906, filed Jun. 26, 2009 claims benefit.

Intracardiac Echocardiographic Guidance & Monitoring During Percutaneous Endomyocardial Gene Injection in Porcine Heart, Seung, et al. (Human Gene Therapy 12:893-903 May 20, 2001).

Invitation to Pay Additional Fees for PCT/US2009/0400984 mailed Jul. 30, 2009, claiming benefit of U.S. Appl. No. 12/117,549, filed May 8, 2008.

Invitation to Pay Additional Fees for PCT/US2009/040979 mailed Jul. 30, 2009 claiming benefit of U.S. Appl. No. 12/117,537, filed May 8, 2008.

Invitation to Pay Additional Fees for PCT/US2009/067486 mailed Mar. 5, 2010, claiming benefit of U.S. Appl. No. 12/336,085, filed Dec. 16, 2008.

Invitation to Pay Additional Fees for PCT/US2010/047241 mailed Jan. 10, 2011, claiming benefit of U.S. Appl. No. 12/844,065, filed Jul. 27, 2010.

Invitation to Pay Additional Fees mailed Mar. 5, 2010 for PCT/US2009/067486 claiming benefit of U.S. Appl. No. 12/336,085, filed Dec. 16, 2008.

Jacob, AL, et al., "A Whole-Body Registration-Free Navigation System for Image-Guided Surgery and Interventional Radiology," Investigative Radiology, vol. 35 No. 5 (May 2000) pp. 279-288.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Jiang, Yuan. "An Impedance-Based Catheter Poisitioning System for Cardiac Mapping and Navigation." IEEE Transactions on Biomedical Engineering, (Aug. 2009) pp. 1963-1970, vol. 56, No. 8.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 717 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51 (1996) pp. 635-638.

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. Car '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble. (1995).

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11.sup.th Annual International Conference, 1989, pp. 0926-0927.

Lavallee, "VI Adaption de la Methodologie a Quelques Applications Cliniques," Chapitre VI, pp. 133-148.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Markowitz, Toby, et al., "Unleaded: The Fluoroless 3D Lead Implant", Presented at Heart Rhythm Society, Denver, CO, (May 2007) 1 pg.

Markowitz, Toby, et al., Abstract Submission, "Unleaded: The Fluoroless 3D Lead Implant", Mar. 2007 2 pgs.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 430-431.

Mazier et al., Chirurgie de la Cotonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al., "Computer Assisted Spine Surgery", Clinical Assisted Spine Surgery, No. 337, pp. 86-96 (1997).

Milstein, S. et al., "Initial Clinical Results of Non-Fluoroscopic Pacemaker Lead Implantation." (pre-presentation abstract) May 14-17, 2008. 2 pgs.

Milstein, S. et al., "Initial Clinical Results of Non-Fluoroscopic Pacemaker Lead Implantation." (poster presentation) May 14-17, 2008. 1 pg.

Muschlitz, Lin, "Ultrasound in the or suite is providing more detailed information to allow less invasive surgeries." Technology—Ultra Sound Surgical Partners (Sep. 2003) Medical Imaging. http://www.imagingeconomics.com/issues/articles/MI_2003-09_03.asp (accessed on Aug. 12, 2010).

Nelder, J.A., et al. "A simplex method for function minimization." vol. 7, Issue 4, (1965) pp. 308-313.The Computer Journal.

Ng, W.S. et al., Robotic Surgery—A First-Hand Experience in Transurethral Resection of the Prostate Surgery, IEEE Eng. in Med. and Biology, pp. 120-125 (Mar. 1993).

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12.sup.th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Enffemung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, Hans. F., Neuronavigation: A Ten-Year Review, Neurosurgery (1996) pp. 329-341.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Savage, George, M.D., Electric Tomography (ET)—A Novel Method for Assessing Myocardial.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microstereoetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. An Comp-Assisted surgery, MRCAS (1995) pp. 185-192.

Smith et al., "Computer Methods for Improved Diagnostic Image Display Applied to Stereotactic Neurosurgery," Automedical, vol. 14, 1992, pp. 371-382.

Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. In Med. and Biol. Soc., vol. 13, No. 1, p. 210 (1991).

Tan, K., Ph.D., et al., a frameless stereotactic approach to neurosurgical planning based on retrospective patient-image registration, J Neurosurgy, vol. 79, pp. 296-303 (Aug. 1993).

The Laitinen Stereotactic System, E2-E6.

Thompson, et al., A System for Anatomical and Functional Mapping of the Human Thalamus, Computers and Biomedical Research, vol. 10, pp. 9-24 (1977).

Trobraugh, J.W., et al.; Frameless Stereotactic Ultrasonography: Method and Applications, Computerized Medical Imaging and Graphics, vol. 18, No. 4, pp. 235-246 (1994).

Vlant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MT Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," lgaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," (1997) pp. 119-128.

Wittkampf, Fred, H.M., et al., "LocaLisa: New Technique for Real-Time 3-Dimensional Localization of Regular Intracardiac Electrodes." Circulation Journal of the American Heart Association, 1999; 99; 13-12-1317.

Wittkampf, Fred., H.M., et al. "Accuracy of the LocaLisa System in Catheter Ablation Procedures." Journal of Electrocardiology vol. 32 Supplement (1999). Heart Lung Institute, University Hospital Utrecht, The Netherlands.

China Office Action for Chinese Application No. 20980121281.3 (PCT/US2009/040998) published as Chinese Publication No. 201250800705320 issued on May 11, 2012 claiming benefit of U.S. Appl. No. 12/425,480, filed Apr. 17, 2009.

International Preliminary Report on Patentability and Written Opinion for PCT/US2010/047241 mailed Mar. 15, 2012 claiming benefit of U.S. Appl. No. 12/844,065, filed Jul. 27, 2010.

* cited by examiner

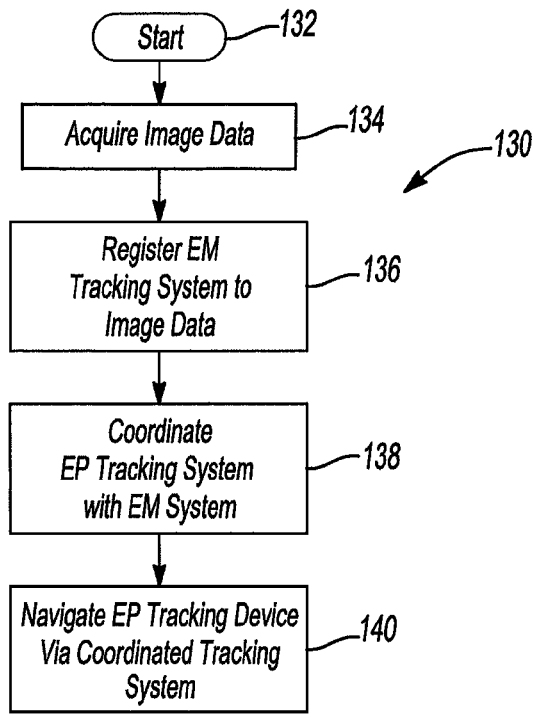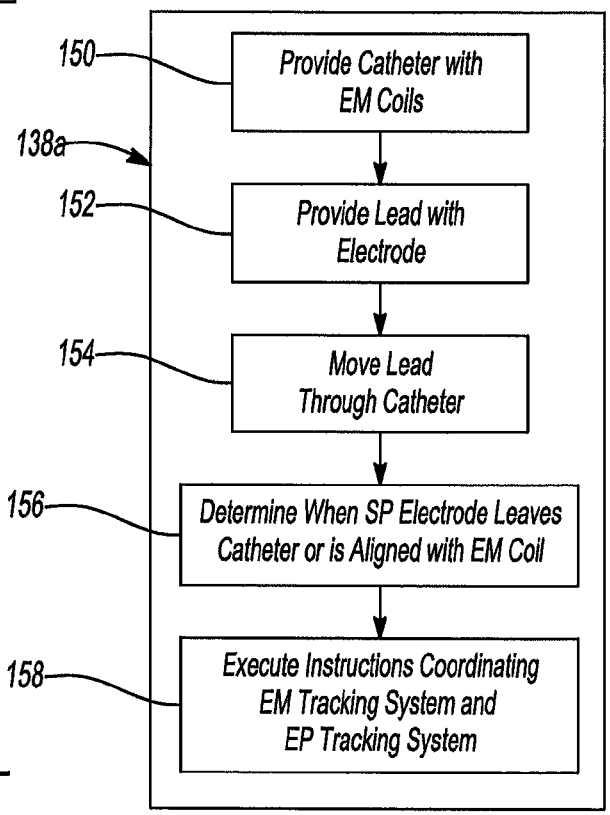

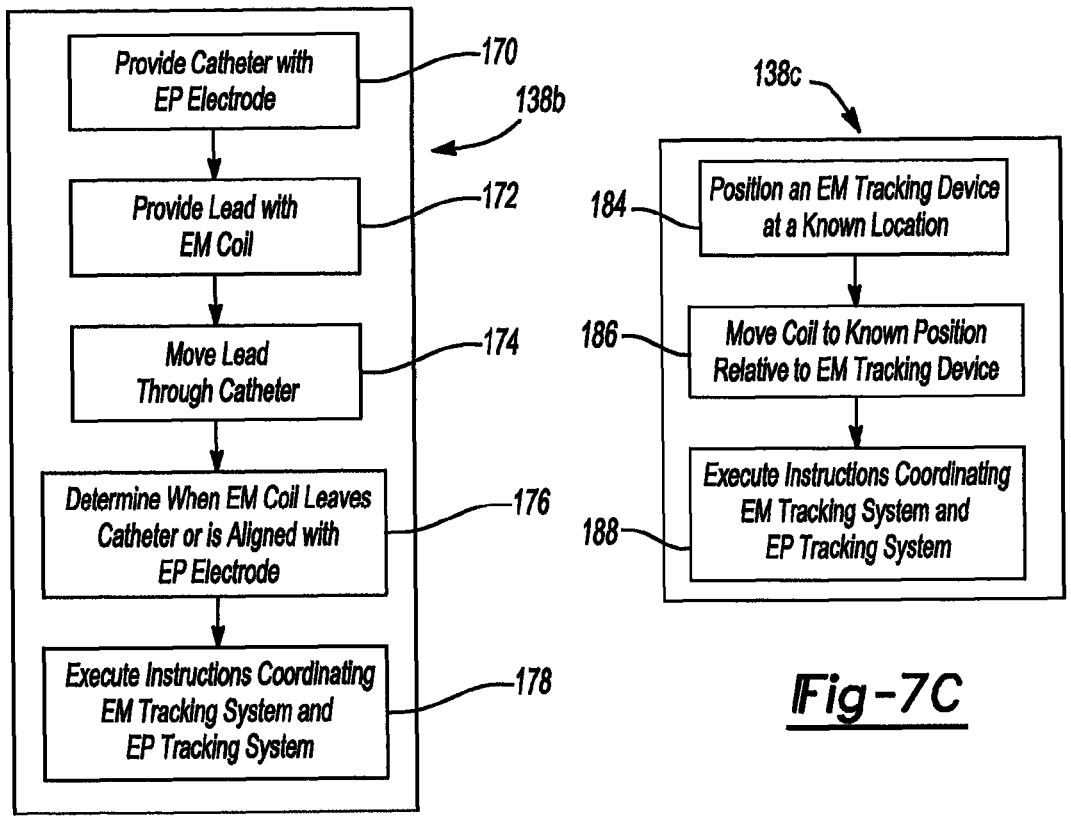
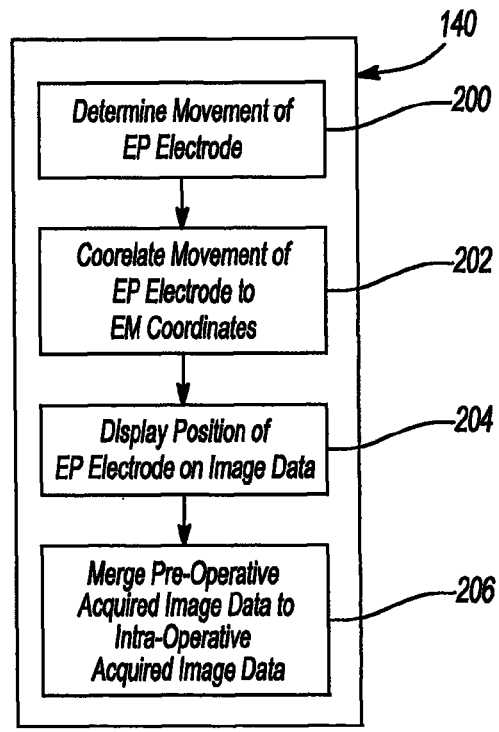

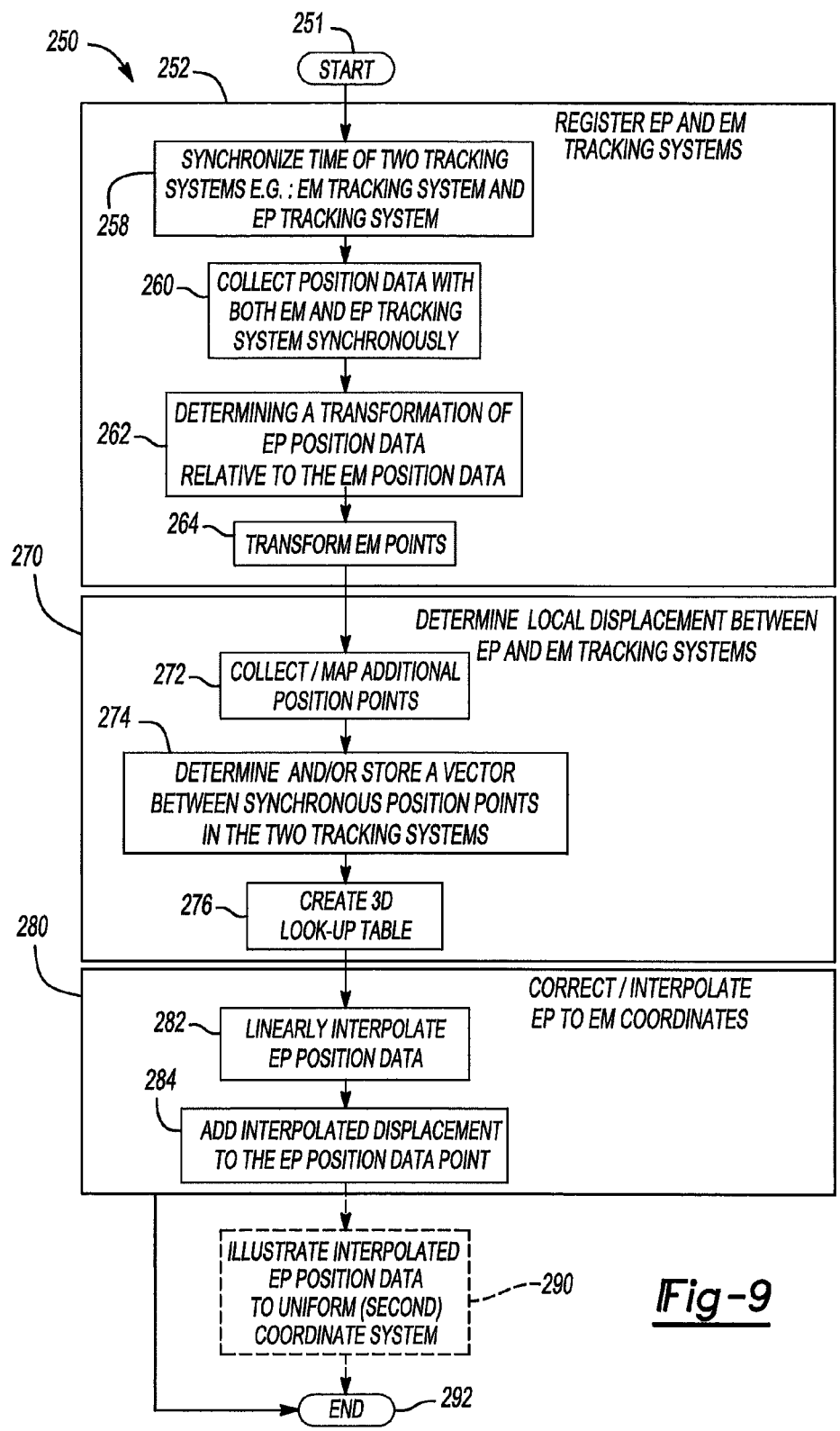

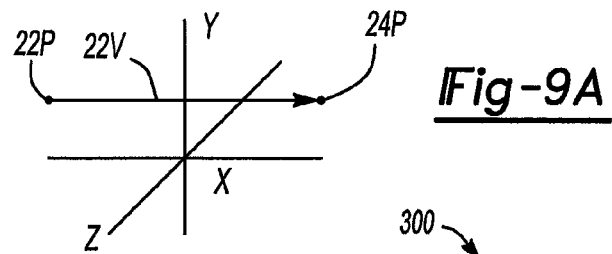
*Fig-9A*
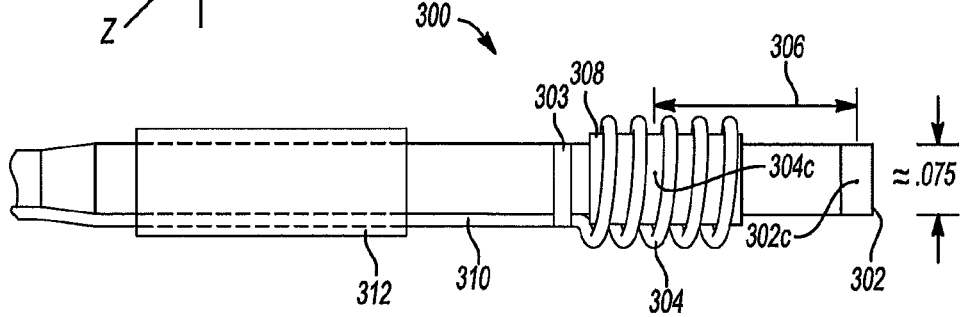
*Fig-10*
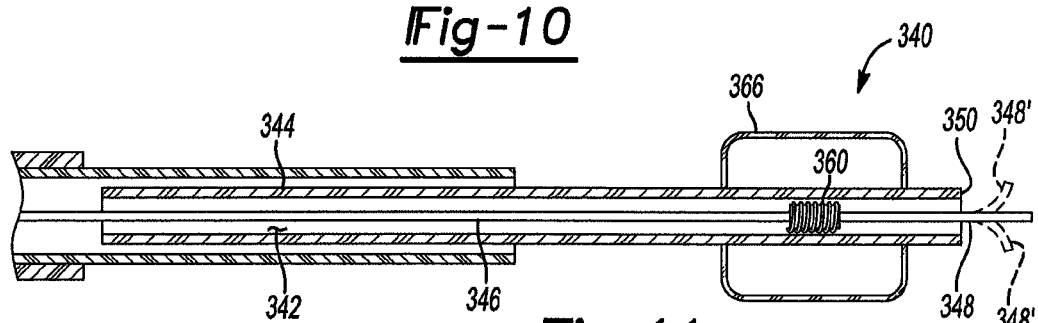
*Fig-11*
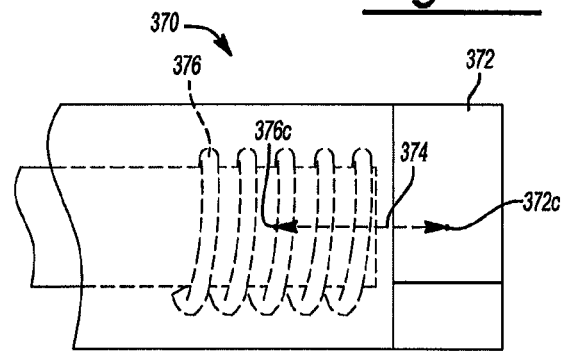
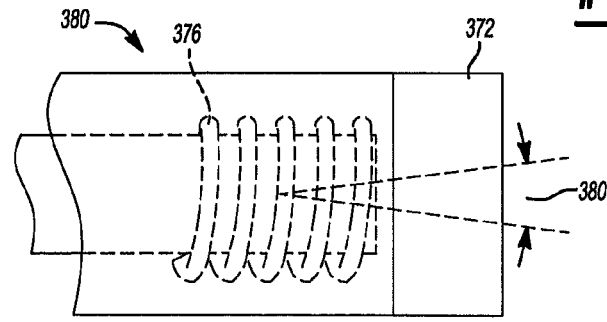
*Fig-12*

COMBINATION LOCALIZATION SYSTEM

CROSS-REFERENCE TO RELATED APPLICATIONS

This application claims the benefit of U.S. Provisional Application No. 61/238,623, filed on Aug. 31, 2009.

This application also includes subject matter similar to that disclosed in U.S. patent application Ser. No. 12/844,061, filed on Jul. 27, 2010, titled "COMBINATION LOCALIZATION SYSTEM."

The entire disclosures of the above applications are incorporated herein by reference.

FIELD

The present disclosure relates generally to a system for localizing a tracked instrument, and particularly to a localization system using two or more modalities for localizing the instrument within a volume.

BACKGROUND

This section provides background information related to the present disclosure which is not necessarily prior art.

A navigation system can be used to track and navigate an instrument within a volume. For example, a navigation system can be used to track an instrument during a procedure, such as a surgical procedure. Various systems can be used to track instruments including electromagnetic systems, optical systems, acoustic systems, and other appropriate systems.

Tracking an instrument can allow for determination of a position of the instrument relative to the patient without directly viewing the instrument within the patient. Various methods can be used to achieve this result, such as directly tracking a particular portion of the instrument exterior to the patient or tracking a distal point of the instrument within the patient.

Differing navigation systems can be used to track different instruments within a patient. For example, a long substantially rigid instrument can be tracked with an optical navigation system that can track a proximal and/or end of the instrument that is external to the patient. Based on determinations, a position of a distal tip or an end of the instrument within the patient can be made. Additionally, navigation systems can use fields, such as electromagnetic fields, to track and navigate a distal portion of an instrument that is within a patient.

SUMMARY

This section provides a general summary of the disclosure, and is not a comprehensive disclosure of its full scope or all of its features.

A navigation system or combination of navigation systems can be used to provide two or more types of navigation or modalities of navigation to navigate a single instrument. The single instrument can be positioned within the patient and tracked. For example, both an Electromagnetic (EM) and Electropotential (EP) tracking systems can be used to navigate an instrument within a patient.

A navigation system can generally include a localizer and a tracking sensor. One skilled in the art will understand that the localizer can either transmit or receive a signal and the tracking sensor can also transmit or receive a signal to allow for a determination of a location of the tracking sensor associated with the surgical instrument. A surgical instrument can have associated therewith two or more tracking sensors that can be used in two or more modalities of navigation. For example, a surgical instrument may include an electrode that can be used with an EP tracking system and can also be associated or moved relative to a tracking sensor that includes an EM coil to be used with an EM tracking system.

An instrument can include one or more tracking sensors to be used with two or more navigation systems during a single procedure. In addition, a method can be used to register the two navigation systems during a single procedure. The registration of the two navigation systems can allow all or a determination of a selected number of points within one navigational domain to coordinate or correspond to all or a selected number of points in a second navigational domain. For example, a surgical instrument can include a single tracking sensor that can be tracked within two navigation modalities. Also, a surgical instrument with a single tracking sensor can be moved relative to a second tracking sensor, where each of the tracking sensors are tracked in different navigation modalities. According to various embodiments, when a first tracking sensor is positioned at a known location relative to a second tracking sensor, a navigation volume or domain of the first navigation system can be registered to a navigation volume or domain of a second navigation system. In this way, a first and second navigation system can be registered for navigating a tracking sensor or a surgical instrument within the two navigation modalities.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is a flow chart of a method of registering two navigation systems;

FIG. 7A-7C are detailed flowcharts of registration of two tracking systems, according to various embodiments;

FIG. 8 is a flowchart illustrating an exemplary method of navigating a registered instrument;

FIG. 9 is a flowchart illustrating a registration or corresponding method for two tracking systems, according to various embodiments;

FIG. 9A is an illustration of placement of position data points;

FIG. 10 is an illustration of an instrument for tracking with two tracking systems, according to various embodiments;

FIG. 11 is an illustration of an instrument for tracking with two tracking systems, according to various embodiments;

FIG. 12 is a schematic illustration of an instrument for tracking with two tracking systems, according to various embodiments;

Corresponding reference numerals indicate corresponding parts throughout the several views of the drawings.

DETAILED DESCRIPTION

Example embodiments will now be described more fully with reference to the accompanying drawings.

Figure 1:
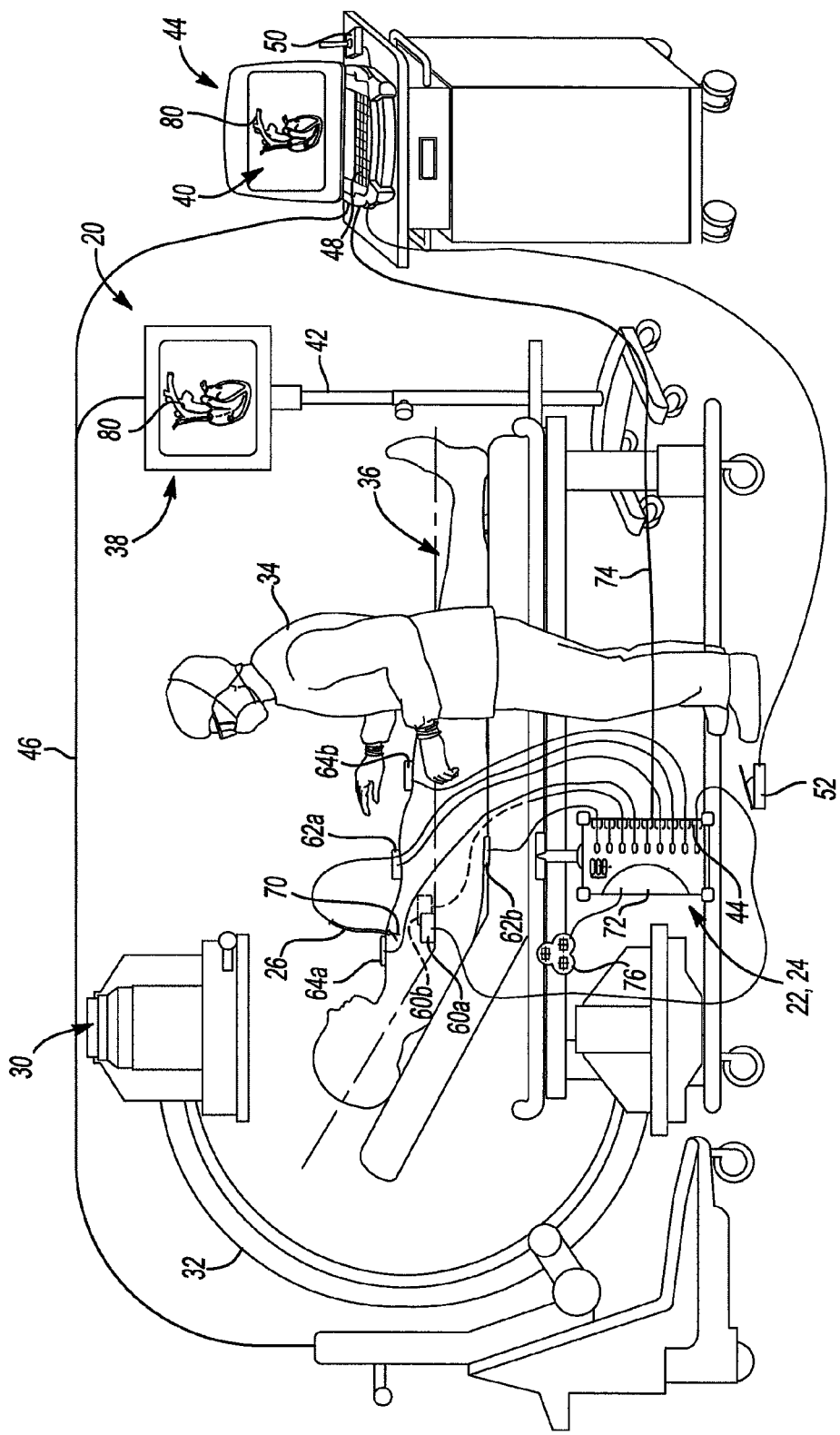
FIG. 1 is an environmental view of a navigation system.

A surgical navigation system 20 is illustrated in FIG. 1. A first tracking system can include an electropotential (EP) tracking system 22. A second tracking system can include an electromagnetic (EM) tracking system 24. Appropriate tracking systems can include those disclosed in U.S. patent application Ser. No. 12/117,537, filed on May 8, 2008 and U.S. Patent Publication No. 2004/0097805, published on May 20, 2004, both incorporated herein by reference. The first and second tracking systems 22, 24 can be used to track a surgical instrument 26. The surgical instrument 26 can be any appropriate instrument, including a lead used as a part of an implantable medical device (IMD) for heart rhythm treatment, neurological treatment, ablation, or other appropriate purposes.

In certain procedures having two tracking systems can be useful. Exemplary procedures using a lead can include left heart applications. In the left heart application an electrode on a lead might not be exposed to blood for position determination with the EP tracking system 24. Accordingly, a position element or tracking sensor associated with the EM tracking system 24 can be used to determine a position of the instrument within the patient 36. Also, the registration of the EM tracking system 24 to image data can be used to assist in illustrating vasculature relative to the heart of the patient 36.

Certain right heart applications also may be more easily tracked with the EP tracking system 22 as opposed to the EM tracking system 24. For example, a stylet including an EM tracking device can be positioned through a lead. In various procedures, however, the stylet can be removed from a portion of the lead to allow the lead to be substantially less rigid and more flexible. Once the stylet is removed from the lead the exact position of the lead may not be trackable with the EM tracking system 24. When the stylet is removed, the lead electrode can be tracked with the EP tracking system 22.

Further, various procedures, such as ablation procedures, use RF energy. RF energy can affect or interfere with the EM tracking system 24. Accordingly, the EP tracking system 22 can be used during or subsequent to RF ablation to continue or maintain tracking of a device.

The surgical navigation system 20 used in the various procedure discussed above or herein, can also include various components in addition to the tracking systems 22, 24, such as an imaging system 30. The imaging system 30 can be any appropriate imaging system and is exemplary illustrated as a fluoroscopic C-arm system 32. Other imaging systems can include computed tomography (CT) imaging systems, magnetic resonance imaging (MRI) systems, and positron emission tomography (PET) imaging systems. The imaging systems 30 can be used by a surgeon 34 to image a patient 36 prior to (preoperatively), during (intraoperatively), or after (postoperatively) a procedure. Imaging the patient 36 can create image data that can be viewed on a display device 38 or a display device 40. The display device 38, 40 can be provided alone, such as on a stand 42 or with a processing system as a part of a workstation or processing system 44. The image data can be transferred from the imaging system 30 through a data transmission system 46, such as a wired or wireless transmission system, to the display devices 38, 40.

The navigation system 20, also including the tracking systems 22, 24 can be incorporated or connected to the processor system 44. The processor system 44 can include human input devices such as a keyboard 48, a joystick or mouse 50, a foot pedal 52 or any other appropriate human input device. Each of the human input devices 48-52 can be connected with the processor system 44 or other systems, such as the imaging system 30, for control or actuation thereof.

The EP tracking system 22 can include components to generate a current in the patient 36. The EP tracking system can include or be based on the Localisa™ intracardiac tracking system sold by Medtronic, Inc. having a place of business in Minneapolis, Minn. The EP tracking system 22 can also include portions disclosed in U.S. Pat. No. 5,697,377 or 5,983,126 to Wittkampf, incorporated herein by reference Briefly, the EP tracking system 22 can include a pair of axis electrodes, which can also be referred to as a localizer, operable to generate a current within a volume, such as the patient 36. The axis electrodes can include three pairs of axis electrodes to generate three substantially orthogonal axes of current within the patient 26 (also see FIG. 4). The axis electrodes can include a first pair 60a, 60b, a second pair 62a, 62b, and a third pair 64a, 64b. The axis can be defined between selected patch pairs, as discussed below, by an alternating current that is generated between any pair of the axis electrodes. For example, the first pair of axis electrodes 60a and 60b can be positioned on a left and right side of the patient 36 to define an X-axis when a current is generated between the two axis electrodes 60a and 60b.

The substantially orthogonal axis of current, defined by the plurality of patches discussed above, can be used to determine or calculate a location of a tracking device 70. The tracking device 70 can include a first or EP tracking device 70a and a second or EM tracking device 70b. The EP tracking system 22 can be used to track the EP tracking device 70a. The first tracking device 70a can sense voltages in the patient 36 based upon the induced currents between any pair of the axis electrodes 60a-64b. The voltages can be related to a position of the first tracking device 70a in the patient 36.

The pairs of axis electrodes 60a-64b can be driven with a generator in a controller 72 that is connected via wires or wirelessly with the axis electrodes 60a-64b. The generator can provide the power to generate the alternating currents in the patient 36 between the respective the axis electrodes 60a-64b. The controller 72 can also include a connection for the instrument 26 to communicate a signal from the tracking device 70 to the controller. The connection with the instrument 26 can be wired or wireless, according to various embodiments. In addition, the controller 72 can include a processor portion or simply be a transmitter to transmit signals from the tracking device 70. Signals can be transmitted from the controller 72 to the processor system 44 with a transmission system 74. The transmission system 74 can be a wired or wireless transmission system.

The EM tracking system 24 can also be associated with the controller 72 or can be provided with a separate controller system. It will be understood that various separate circuitry portions may be provided in the controller 72 to generate or operate the EP tracking system 22 or the EM tracking system 24.

The EM tracking system 24 includes an EM localizer 76 that can be positioned relative to the patient 36. The EM tracking system can include the AxiEM™ electromagnetic tracking system sold by Medtronic Navigation, Inc. having a place of business in Colorado, USA. The localizer 76 can generate an electromagnetic field that is sensed by the EM tracking device 70b. Alternatively, the EM tracking device 70b can generate a field that is sensed by the localizer 76.

A localizer can be used as a part of a tracking system to determine the location of the tracking device 70. For example, the localizer 76 can be interconnected with the controller 72 to transmit a signal to the processor system 44 regarding the position of the EM tracking device 70b. The axis electrodes 60a-64b can be a localizer that induces axes of current in the patient 36 to localize the EP tracking device 70a. Accordingly, the localizer can refer to a portion of the tracking system which can be exterior to the volume, such as the patient 36, that is used to determine a position of the tracking device 70.

According to various embodiments, the localizer devices, including the EM localizer 76 and the axis electrodes 60a-64b, can be used to define a navigation domain in a patient space of the patient 36. Patient space can be the physical space that is being operated on during the operative procedure. The patient space can also include the navigated space through which the surgical instrument 26 is being navigated. Image space can be defined by image data 80 that is displayed on the display devices 38, 40. Image data 80 can include any appropriate image data, such as image data of a heart 84 (FIG. 4) of the patient 36. The image data 80 displayed on the display devices 38, 40 can also include atlas data. Atlas data can include statistical or historical data. The atlas data can be registered or morphed to the patient image data or patient space. It will be understood that atlas data may be used in an imageless navigation system. For example, an imageless navigation system may not require the acquisition of image data of the patient 36.

The patient space can be registered to the image space of the image data 80 according to any appropriate technique, including those discussed herein. Generally, however, the patient space is registered to the image data 80 to allow for displaying or a super imposing an icon or representation of a tracked device, for example the surgical instrument 26, over the image data 80 on the display device 38, 40. Registration generally allows for a transformation of the image data to the patient space. Various registration techniques can include contour matching, fiducial or point matching, automatic registration, or any other appropriate registration. For example, various landmarks or fiducials can be identified in the image data 80 and the same fiducials or landmarks can be identified in the patient 36, such as within the heart 84. The image data 80 can then be transformed to the patient space of the patient 36 so that a proper location of a superimposed icon 26i can be shown relative to the image data 80 of the heart 84. Registration techniques can include those discussed in the U.S. patent applications incorporated above. In addition, as discussed herein, the EP tracking system 22 can be registered to the EM tracking system 24. The registration of the EP tracking system 22 to the EM tracking system 24 can allow navigation of the EP tracking device 70a with the image data 80.

Figure 2:
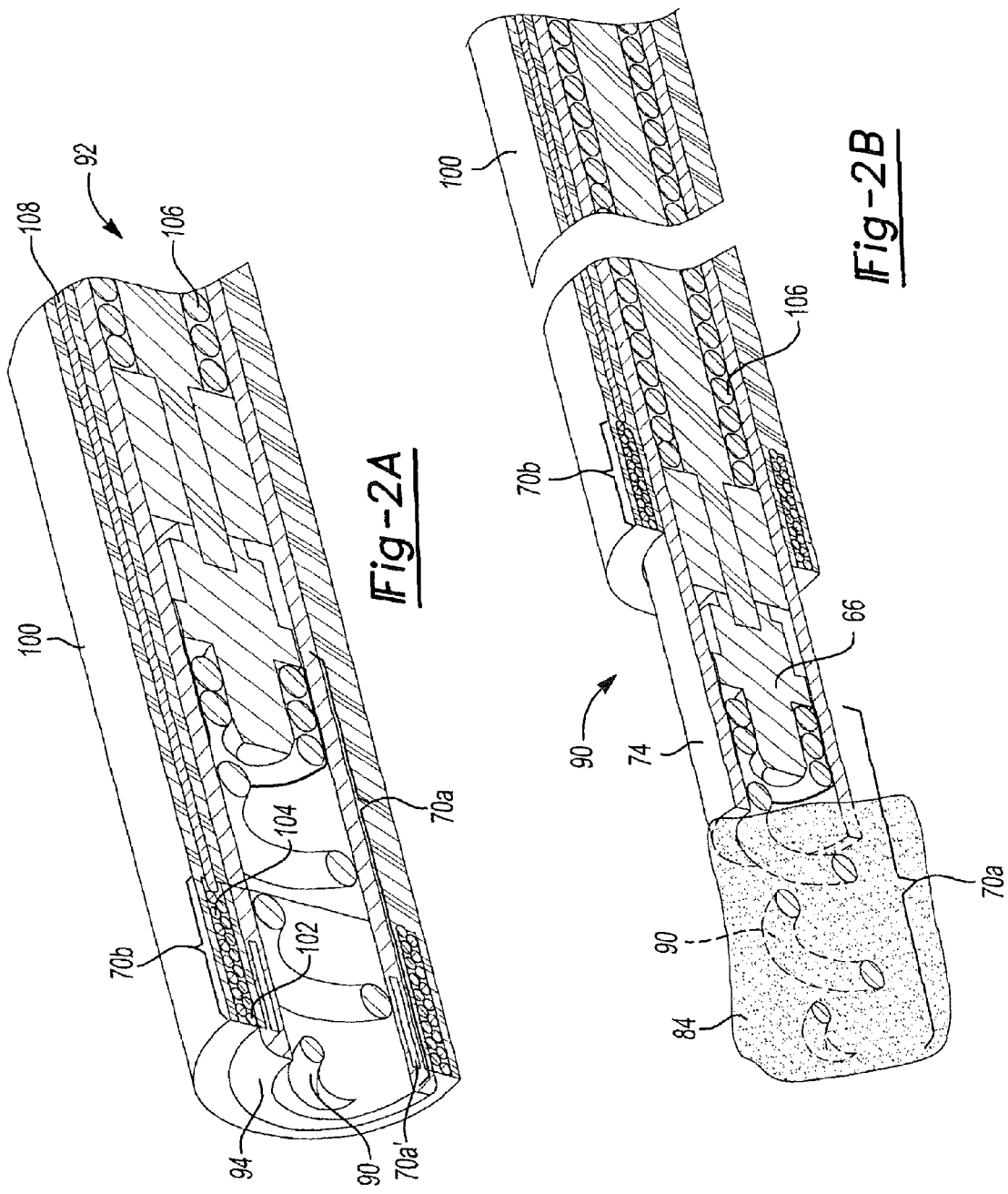
FIG. 2A is a detailed cross-section view of an instrument, according to various embodiments.
FIG. 2B is a detailed cross-section and environmental view of an instrument, according to various embodiments.

Turning to FIGS. 2A and 2B, the tracking device 70 can include the two tracking devices 70a and 70b. The first tracking device 70a can be a single electrode or a tip electrode 90 or ring electrode (not illustrated) of a lead assembly 92. The lead assembly 92 can be a lead for any appropriate device, such as a pacing or defibrillator system. The lead assembly 92 can be positioned or delivered within a sheath 94 according to generally known lead assemblies, such as the such as the Attain family of catheters sold by Medtronic Inc., having a place of business in Minneapolis, Minn.

The lead assembly 92 can be positioned within the patient 36, such as relative to the heart 84, with a catheter assembly 100. The catheter assembly 100 can be any appropriate configuration. The catheter 100 can include a body molded to substantially define a cannula. The catheter assembly 100 can include the second tracking device 70b. The second tracking device 70b can include a first coil 102 and a second coil 104, or any appropriate number of coils, as part of the EM tracking device 70b. The coils can be coiled with any appropriate configuration, such as around substantially orthogonal axes to one another. The second tracking device 70b, however, can sense an electromagnetic field generated with the localizer 76 or generate an electromagnetic field that is sensed by the localizer 76.

The two tracking devices 70a, 70b can be used with respective tracking systems 22, 24. The first tracking device 70a can sense a voltage or determine bioimpedance (such as an impedance of a tissue of the patient 36) because of the induced currents from the axis electrodes 60a-64b. The currents generate voltages that can be sensed with the EP tracking device 70a. The voltages sensed by the EP tracking device 70a can be transmitted to the controller 72 with an appropriate communication line, such as a conductor 106. The conductor 106 can be conductively coupled to the EP tracking device 70a. It will be understood that although the EP tracking device 70a is illustrated as the tip electrode 90 of the lead assembly 92, that the EP tracking device 70a can also include an alternative EP tracking device 70a' formed as a part of the sheath 94. Regardless of the position of the EP tracking device 70a, its contact (e.g. by removal of a portion of insulation around the electrode) with a conductive medium or electrolyte of the patient 36 can increase and provide efficiency of detecting an appropriate voltage. The voltage sensed by the EP tracking device 70a can be used to determine the position of the EP tracking device 70a as discussed further herein and also described in the above incorporated U.S. patent applications and patents.

The second tracking device 70b, according to various embodiments, can sense an electromagnetic field generated by the localizer 76. For example, a current can be induced in one or more of the coils 102, 104 that is dependent upon the position of the coils 102, 104 in a portion of the electromagnetic field. The generated current can be sent as a signal along a transmission line 108 to the controller 72.

As discussed further herein, and illustrated in FIG. 2B, the lead assembly 92 can be moved relative to tissue of the heart 84 to position the distal tip electrode 90 into the heart 84. When positioning the distal tip electrode 90 into the heart 84, the sheath 94 and the tip 90, which can include the first tracking device 70a, can move relative to the catheter assembly 100. Moving the first tracking device 70a relative to the catheter assembly 100 moves the first tracking device 70a relative to the second tracking device 70b. As discussed herein, this can be used to determine the location of the first tracking device 70a relative to the second tracking device 70b for registration of the EP tracking system 22 and the EM tracking system 24. This determination can be used to track the first tracking device 70a relative to the patient 36 and with the registered image data 80.

In addition, the tracking devices 70a and 70b could be the same coil of wire or conductive material provided with different insulation characteristics. For example, the loops or turns of the tracking device 70a can be electrically separated from the loops or turns of wire for the second tracking device 70b. Both sets of loops can be of the same length of wire over top one another. The conductive media or loops of the first tracking device 70a can be external and exposed to the patient to sense or measure the voltage in the patient. The second portion of the loops can be isolated from the patient and insulated, but they can, along with the first portion, sense the field of the EM tracking system 24.

Figure 3:
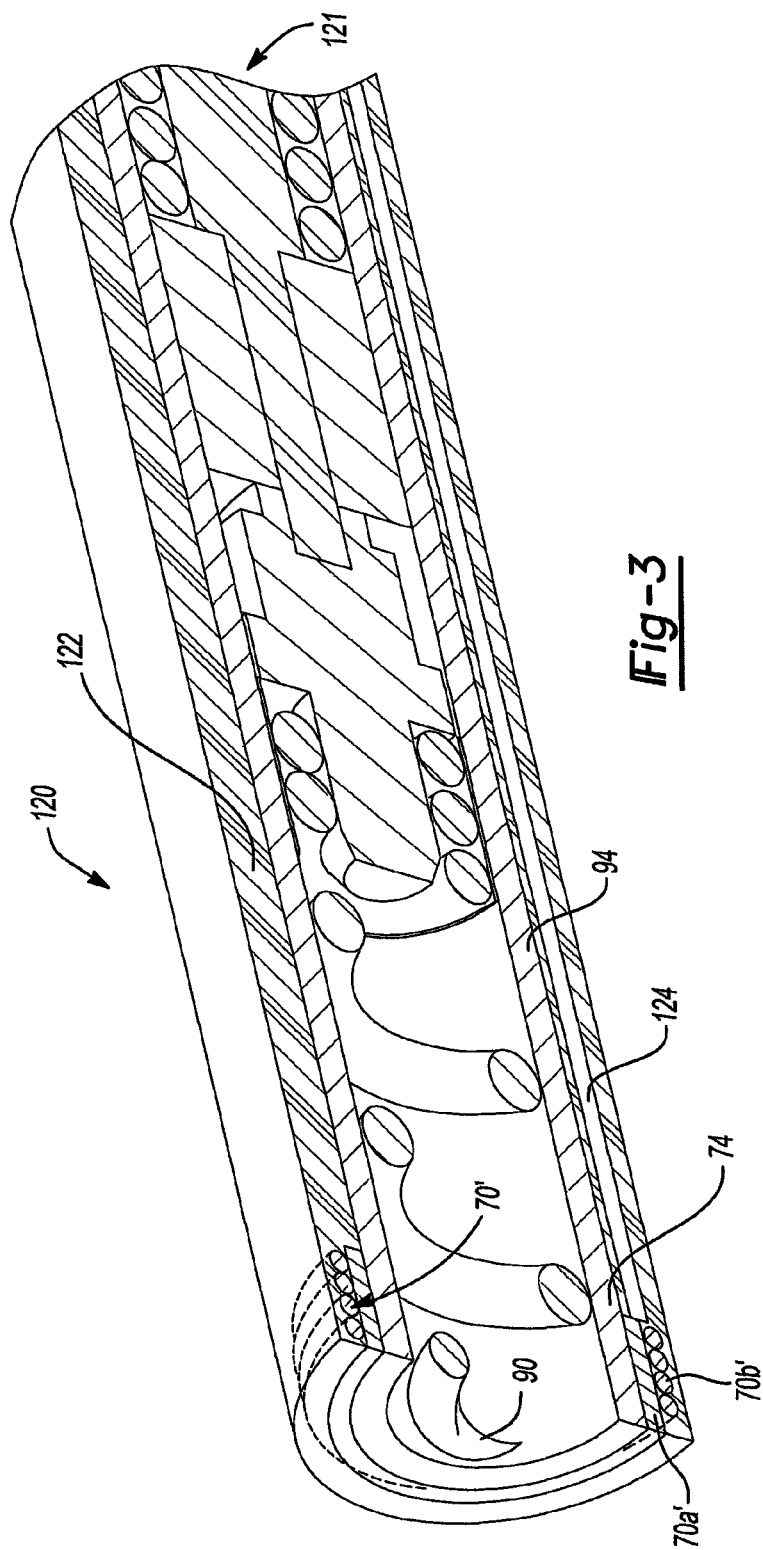
FIG. 3 is a detailed cross-section view of an instrument, according to various embodiments.

Turning to FIG. 3, an instrument 120, according to various embodiments, is illustrated. The instrument 120 can include a lead assembly 121 substantially similar to the lead assembly 92 discussed above, including a tip electrode 90 and a sheath 94. The instrument 120 can also include a catheter assembly 122. The lead assembly 121, including the distal tip 90 and the sheath 94 can be moved relative to the catheter assembly 122.

The catheter assembly 122 can include the tracking device 70' as a single unit or device including an EP tracking device 70a' and one or more windings of an EM tracking device 70b'. The EM tracking device 70b' can be positioned substantially over or around the EP tracking device 70a'. The EP tracking device 70a' can include an annular ring that is molded into or formed with the catheter assembly 122. The EP tracking device 70a' can be used with the EP tracking system 22 similar to the distal tip electrode 90 of the lead assembly 92. The EM tracking device 70b' can be used with the EM tracking system 24 similar to the windings 102, 104 of the EM tracking device 70b. Nevertheless, the EP tracking device 70a' and the EM tracking device 70b' can be positioned substantially atop one another. This allows for the tracked position of the EP tracking device 70a' and the tracked position of the EM tracking device 70b' to be substantially coincident throughout a tracked procedure. A signal from either of the EP tracking device 70a' or the EM tracking device 70b' can be transmitted along or with a communication system 124. For example, the EM tracking device 70b' can include a wired or wireless transmission system.

Again, it will be understood, that the tracking device 70' can be tracked with the two tracking systems 22, 24. As discussed above, the electrode of the EP tracking device 70a' can sense the voltages within the patient 36. The EM tracking device 70b' can sense a magnetic field or electromagnetic field or transmit a magnetic field or electromagnetic field. Accordingly, the single tracking device 70' can be used with two or more tracking systems 22, 24 to determine a location of the tracking device 70' and the catheter and lead assembly 120. It will be further understood that the tip electrode 90 of the lead assembly 121 can also be used as the EP tracking device with the EP tracking system 22.

Figure 4:
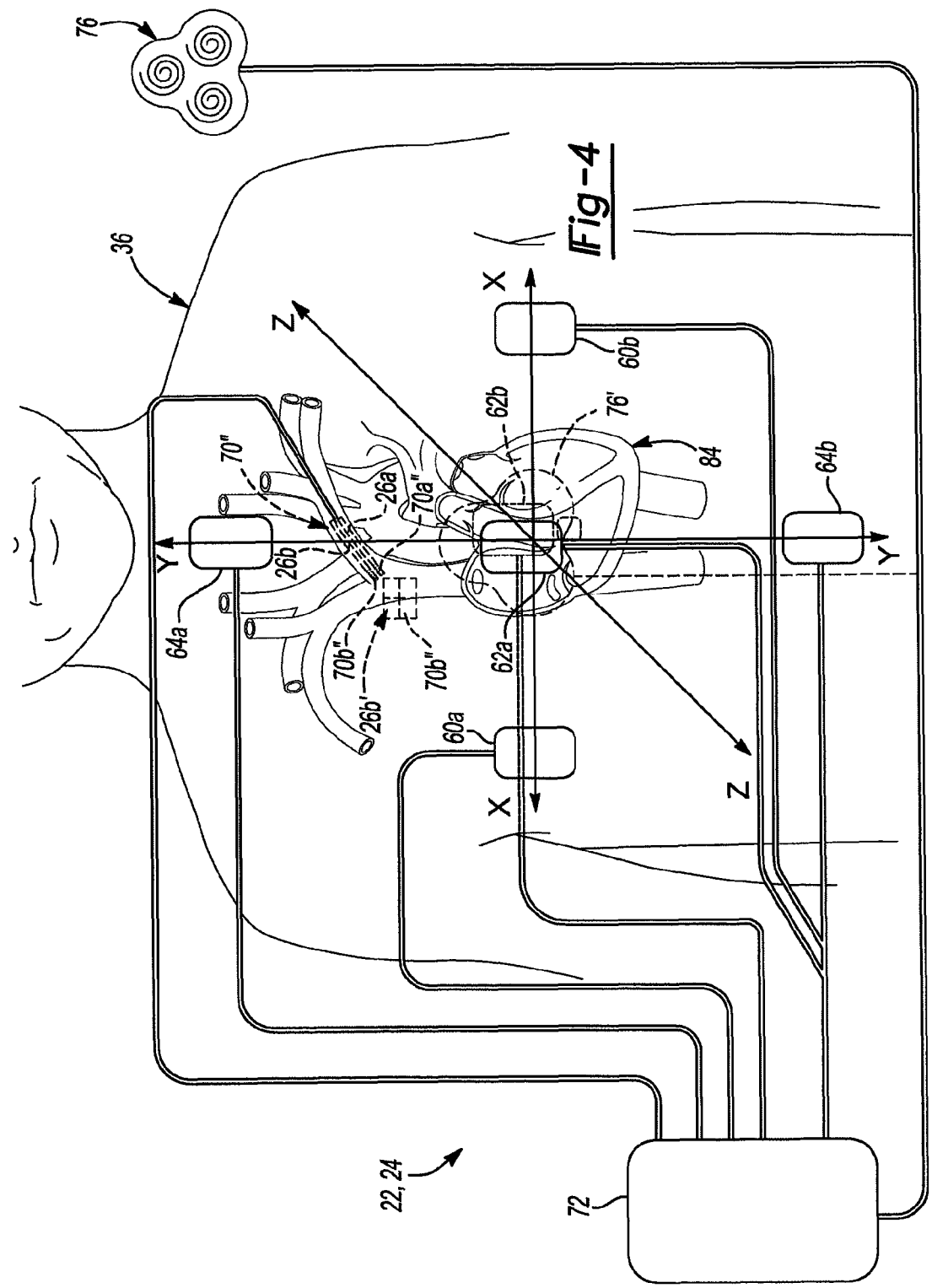
FIG. 4 is an environmental view of a navigation system, according to various embodiments.

With reference to FIG. 4, a tracking device 70" can include an EP tracking device 70a" and an EM tracking device 70b". The EP tracking device 70a" can be positioned on a first instrument portion 26a and the EM tracking device 70b" can be positioned on a second instrument portion 26b. The two instrument portions 26a, 26b can be positioned within the patient 36. Alternately, one of the two instrument portions 26 can be positioned relative to the patient 36 in any appropriate manner. For example, the second instrument portion 26b including the EM tracking device 70b" can be positioned on an exterior surface of the patient 36 or be implanted as a fiducial or dynamic reference frame in the patient 36, such as fixed relative to the heart 84.

The two tracking devices 70a" and 70b" can be moved relative to one another during an operative procedure. For example, if both of the tracking devices 70a" and 70b" are positioned on two separate and moveable instruments 26a, 26b they can be moved to a known position relative to one another within the patient 36 during an operative procedure. Alternatively, if the second instrument 26b is positioned at a fixed location relative to the patient 36, the first instrument portion 26a can be moved to a known position relative to the second instrument portion 26b during an operative procedure. For example, fluoroscopic or ultrasound imaging, such as with the imaging system 30, can be used to confirm or determine the known position of the first surgical instrument 26a and the second instrument 26b. Accordingly, during a second procedure, a position of the EP tracking device 70a" and the EM tracking device 70b" can be determined.

A location of the EP tracking device 70a" can be determined with the EP tracking system 22. The EM tracking system 24 can be used to determine the location of the EM tracking device 70b". As discussed further herein, the determined location of the two tracking devices 70a", 70b" can be used to register the EP tracking system 22 and the EM tracking system 24. The tracked position of the two instruments 26a, 26b can be used for illustration of an icon representing one or both of the instruments 26a, 26b on the display devices 38, 40 relative to the image data 80.

Turning reference to FIG. 5, a flow chart or navigation method for registering or coordinating a dual tracking system 130 is illustrated. The navigation method 130 is illustrated briefly in FIG. 5 and further detailed in FIGS. 7A-7C and 8. The method of using a two tracking system navigation system will be discussed in an exemplary embodiment herein. It will be understood, however, that a navigation system including two or more tracking systems can be used according to various embodiments, including those discussed above. The assembly 92, however, is discussed as an exemplary embodiment.

The navigation method 130, as discussed in detail herein, allows for registration of the EP tracking system 22 to the EM tracking system 24 and further to the image data 80. The EM tracking system 24 can be registered to the image data 80, as discussed herein, including registering the navigation domain of the EM tracking system 24 with the image space. The EP tracking system 22, including the navigation domain of the EP tracking system 22, can be registered to the EM tracking system 24, including the EM navigation domain, according to various embodiments, such as using the devices discussed above. The registration of the EP tracking system 22 to the EM tracking system 24 can allow the EP tracking system 22 to be registered to the image data 80.

The navigation method 130 can include starting in start block 132. The image data 80 can then be acquired in block 134. In addition, with reference to FIG. 6, the image data 80 can be displayed on the display device 40. As discussed above, an icon 92i can be superimposed on the image data 80 to represent a location of an appropriate instrument, such as the surgical instrument 26. The image data 80 can include three dimensional or two dimensional image data that is acquired for representation or illustration of a portion of the patient 36. It will be further understood that the image data 80 acquired in block 134 can be image data that is acquired preoperatively, intraoperatively, or at any appropriate time. It may also include a combination of preoperative and intraoperative image data. For example, preoperative image data can be merged or registered with intraoperative image data according to any appropriate technique. For example, 2D to 3D image registration can occur as described in U.S. patent application Ser. No. 10/644,680 filed Aug. 20, 2003, incorporated herein by reference.

The acquired image data can be stored or transferred to the processor system 44 which is a part of the navigation system 20 for use in illustrating a tracked location of the surgical instrument 26 relative to the patient 36. To assist in illustrating the correct location of the surgical instrument 26 relative to the patient 36, the patient space generally defined by the tracking system 22, 24, can be registered to the image data 80 or image space in block 136. The registration of the image data 80 to the patient space can be with any appropriate method, as discussed above.

The registration of the image data 80 to the patient space can be performed with the EM tracking system 24. The EM tracking system 24, including the localizer 76, can generate a field and navigation space which can be substantially known and is definable in Euclidean coordinates. The known navigation space can be efficiently and directly registered to Euclidean coordinates of the image data 80. The known field of the EM localizer 76 allows a detected change in the field sensed with the EM localizer 76 to be directly related to a distinct position or movement in the field at substantially all points in the field. In other words, a detected movement of the EM tracking device 70b generally results in the same signal change regardless of the position of the EM tracking device 70b within the field generated by the EM localizer 76. Also, every space in the EM navigation domain is known due to the uniform electromagnetic field. Accordingly, a coordinate system identified or defined by the EM tracking system 24 can be substantially known and efficiently applied to the coordinate system of the image data 80.

The registration of the image data 80 to the patient space identified with the EM tracking system 24 can be performed in any appropriate manner. As discussed above, point, contour, or any other appropriate registration processes can be used. For example, the EM tracking device 70b can be positioned relative to known fiducials or landmarks within the patient 36 and similar or related landmarks or fiducials can be identified in the image data 80. The processor system 44, or any appropriate processor system, can then be used to register the points in the image data 80 to the points of the patient space. Once the registration has occurred, the image data 80 is registered to the patient space identified or within the navigation space defined by the EM tracking system 24.

The EM tracking system 24 can be registered to the EP tracking system 22 in block 138. The registration or coordination between the EM tracking system 24 and the EP tracking system 22 can occur at any appropriate time, such as before or after the EM tracking system 24 is registered to the image data in block 136. The EP tracking system 22 can be registered to the EM tracking system 24 in block 138 in any appropriate manner. As discussed further herein, exemplary registration systems 138a, 138b, and 138c are illustrated and described in greater detail in relation to FIGS. 7A-7C. Once the EP tracking system 22 is registered with the EM tracking system 24, navigation of the instrument 26 with only the EP tracking device 70a can be done in block 140. The navigation with the EP tracking device 70a can be done and a position of the instrument 26 including the tracking device 70a can be navigated relative to the image data 80 due to the registration of the EP tracking system 22 and the EM tracking system 24 in block 138. Accordingly, navigation using only the EP tracking system 22 can occur in block 140.

Figure 6:
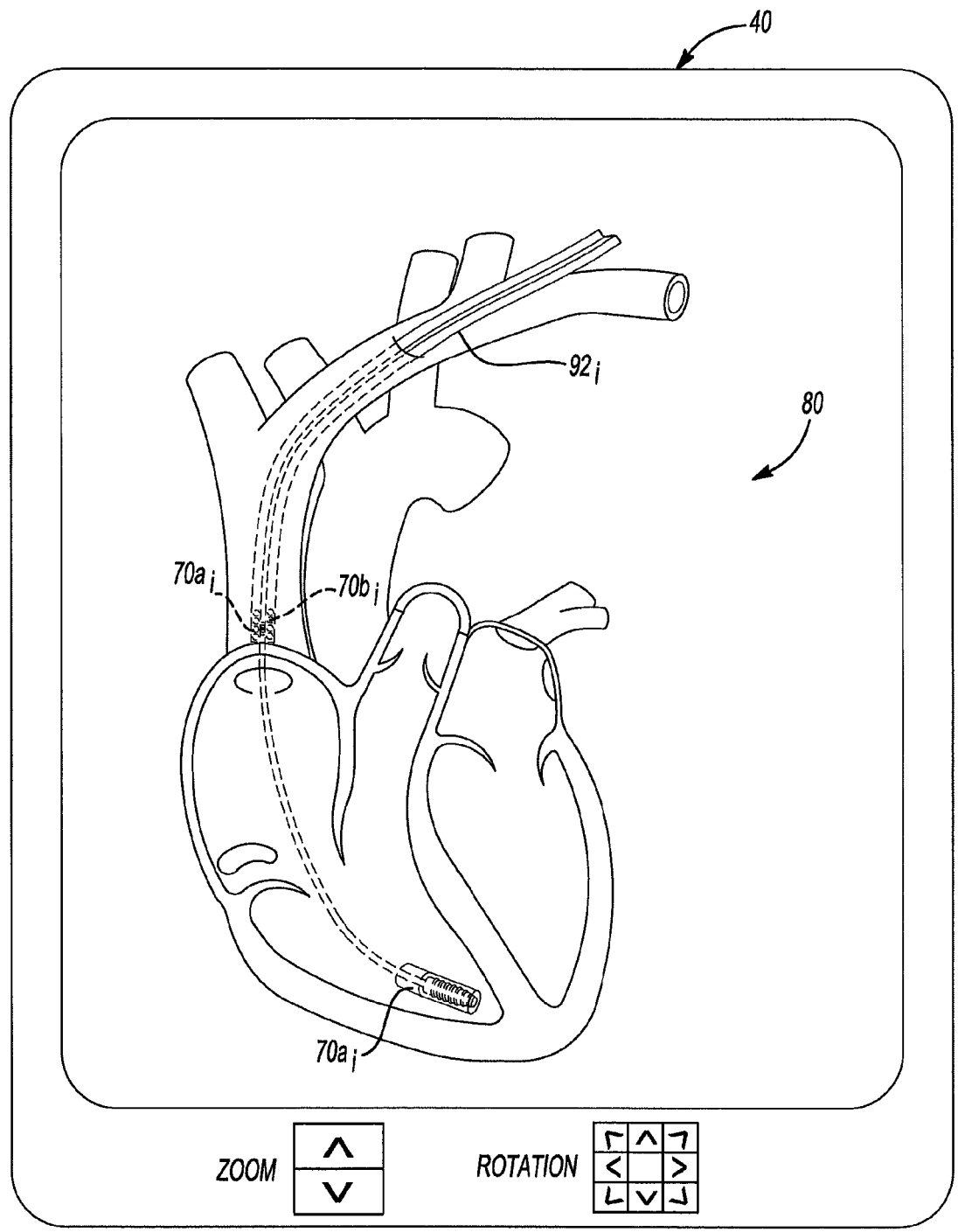
FIG. 6 is a view of image data and icons displayed relative to the image data, according to various embodiments.

With continuing reference to FIGS. 5 and 6 and additional reference to FIG. 7A, registration of the EM tracking system and the EP tracking system, according to various embodiments, is illustrated in block 138a. As discussed above, the lead assembly 92 can include the EP tracking device 70a that can be defined by the tip electrode 90 of the lead 92. The catheter 100 can include one or more coils 102, 104 of the EM tracking device 70b. As illustrated in FIG. 6, the EM tracking device 70b can be used to register the image data 80 to the patient space of the patient 36.

Once the registration has occurred in block 136, then the EP tracking system 22 can be registered with the EM tracking system 24 in block 138a, illustrated in FIG. 7A. A lead or instrument including an EP electrode can be provided in block 152. The EP electrode can be a distal tip electrode of the lead or can be provided in any other portion, such as in the sheath 94. For example, as illustrated in FIG. 2A, the alternative EP tracking device 70a' can be provided in the sheath 94. Regardless of the position of the electrode it can be used as the EP tracking device 70a and it can be positioned relative to the EM tracking device 70b that is positioned within the catheter 100. In addition, as illustrated in FIG. 2B, the lead including the EP tracking device 70a can be moved relative to the catheter 100 in block 154.

When moving the lead relative to the catheter 100, it can be determined when the EP tracking device 70a moves past or is near the coils 102, 104 of the EM tracking device 70b in block 156. Various mechanisms can be used to determine when the EP electrode 70a moves past the EM tracking device 70b. For example, a change in impedance, measured voltage, or other determinations can be measured with the EL electrode 70a and used to determine when the EP electrode is next to or immediately past the EM tracking device 70b.

When the determination is made that the EP tracking device 70a has been positioned relative to the EM tracking device 70b, such as substantially in the same position, a registration of the EM tracking system 24 and the EP tracking system 22 can occur in block 158. The registration can occur by substantially coordinating or registering the EP tracking system 22 and the EM tracking system 24. In other words, because the EP tracking system 22 can be used to determine the position of the EP tracking device 70a and the EM tracking system 24 can be used to determine the position of the EM tracking device 70b these two positions or points in patient space can be identified as the same. Accordingly, the navigation space of the EP tracking system 22 can be overlaid or registered with the navigation space of the EM tracking system 24.

The coordination or registration between the EP tracking system 22 and the EM tracking system 24 can be performed by acquiring a selected number of points that are identical or at known locations relative to one another, as discussed above, with both of the tracking systems. For example, at least three corresponding points may be acquired though more points may be used to actually model or characterize the non-orthogonal or known navigation space defined by the EP tracking system 22. Less information may be necessary in a local or small region than would be needed for a larger space, such as an entire navigation space. Once points with both of the tracking systems have been acquired a curvature model, such as a spline model, can be used to model the EP tracking system 22 coordinate system or navigation space. Other appropriate modeling calculations could also be used to computationally coordinate the EP tracking system 22 and the EM tracking system 24.

Once the EM tracking system 24 and the EP tracking system 22 have been registered, movement of the EP tracking device 70a within the patient space of the patient 36 can be illustrated superimposed on the image data 80. As illustrated in FIG. 6, icons illustrating the first tracking device 70ai and second tracking device 70bi can be illustrated and superimposed on the image data 80. Once registration has occurred, however, the EP tracking device icon 70ai, illustrating the position of the EP tracking device 70a, can be illustrated separate from the EM tracking device icon 70bi, representing the position of the EM tracking device 70b, but correctly related to the image data 80. It will be understood that an icon 92i can represent generally the surgical instrument 26, or any portion thereof, and not only the tracking devices. The position of the surgical instrument, however, can be identified or determined based upon the tracked position of the tracking device 70.

Registration of the EP tracking system 22 with of the second navigation space, such as that of the EM tracking system 24, can allow for image navigation of the instrument 26 tracked with only the EP tracking system 22. The navigation space of the EP tracking system 22 may not be substantially uniform or strictly aligned with the coordinates that were used to acquire the image data 80. For example, the tissue of the patient 36 may not be substantially uniform impedance. For example, the impedance of muscle tissue may be substantially different from the impedance of blood or other electrolyte. Accordingly, a particular change in voltage may not always be related to a single physical quantity of movement amount of the EP tracking device 70a. Movement of the EP tracking device 70a within the patient 36, however, can be measured using the EP tracking system 22 once it is registered with a tracking system, such as the EM tracking system 24, which can be registered to the image data 80. A registered position of the EP tracking device 70a can be superimposed on the image data 80. Therefore, a position of the EP tracking device 70a can be superimposed on the image data 80 even if a non-uniform navigation space is generated with the EP tracking system 22.

Returning reference to FIG. 7B, registering the EP tracking system 22 and the EM tracking system 24 can be achieved with registration method 138b. According to the registration method 138b, a catheter can be provided with an EP electrode as the EP tracking device 70a in block 170. A lead assembly can be provided with the EM tracking device 70b in block 172. The lead can then be moved relative to the catheter in block 174. A determination can be made when the EM tracking device 70b is aligned with or at a selected and known position relative to the EP tracking device 70a in block 176. A registration of the EM tracking system 24 and the EP tracking system 22 can then occur in block 178. The registration method 138b can be substantially similar to the registration method 138a (illustrated in FIG. 7A) save that the EP electrode is positioned in the catheter 100 and the EM tracking device 70b is positioned on the lead. Therefore, registration can occur in substantially the same way and tracking of the EP tracking device 70a can occur and superimposition of a position of the EP tracking device 70a can be illustrated relative to the image data 80.

Turning to FIG. 7C, a registration method 138c is illustrated. The registration method 138c can include positioning the EM tracking device 70b at a known location in the patient 36 or other navigable space in block 184. The EM tracking device 70b can be any appropriate device, for example the second tracked instrument 26b illustrated in FIG. 4. The second tracked device 26b can be a second instrument moved relative to the patient 36, a dynamic reference frame (DRF) fixed relative to the patient 36, or any appropriate device including the EM tracking device 70b. For example, the DRF 26b' can be positioned relative to the patient 36 at a fixed and known location. The known location of the DRF 26b' can be determined in any appropriate manner. For example, a registration probe (not illustrated) can be moved relative to the DRF 26b' to determine the location of the DRF 26b'. In addition, the DRF 26b' can be positioned or include a fiducial that is identified in the image data 80 to allow for identification and registration to the image data 80. Alternatively, if the second instrument 26b is a moveable instrument, it can be moved to a landmark that can also be identified within the image data 80.

When the second tracked device 26b, 26b' is identified relative to the image data 80 and the EM tracking system 24 is registered to the image data 80, the first tracked instrument 26a including the EP tracking device 70a can be moved relative to the second tracked device 26b, 26b'. For example, the first instrument 26a, illustrated in FIG. 4, can move to the location of the DRF 26b' in block 186. Once the first tracked instrument 26a is at the same position as the DRF 26b', registration of the EM tracking system 24 and the EP tracking system 22 can occur in block 188. As discussed above, the location of the two tracking devices 70a, 70b can be determined to be substantially identical when they are positioned next to each other to allow for registration of the two tracking systems 22, 24.

It will be further understood that when two tracked instruments 26a, 26b are provided, they can be positioned at a known position and orientation relative to one another to allow for registration to occur in block 188. For example, the first tracked instrument 26a can be positioned at a known position and orientation relative to the DRF 26b'. The DRF 26b' can be tracked with one of the two tracking systems and the first tracked instrument 26a with the other tracking system and registration can occur. In other words, knowing a position and orientation of the DRF 26b' and position and orientation of the EP tracking device 70a relative to the DRF 26b' can allow for registration of the two tracking systems 22, 24 even if the two tracking devices 70a, 70b are not in substantially identical locations. As discussed above, imaging systems can be used to determine or identify the known locations of the two tracking devices 70a, 70b.

Registration of the EP tracking system 22 and the EM tracking system 24 can also occur by providing the EP tracking device 70a and the EM tracking device 70b substantially at the same position on the tracked instrument 26, as illustrated with the instrument 120 in FIG. 3. When the tracking device 70 has substantially only one location for both the EP tracking system 22 and the EM tracking system 24 a complex determination of registration is not otherwise required, including positioning the EP tracking device 70a relative to the EM tracking device 70b. Because the two tracking devices are at substantially the same or corresponding point, the tracked position of the EM tracking device 70b with the EM tracking system 24 can be used to correspond the position of the EP tracking device 70a inherently since all positions determined with the EM tracking device 70b are inherently registered with the EP tracking device 70a. Therefore, the coordinate system of the EM tracking system 24 can be used to illustrate a position of the EP tracking device 70a on the image data 80 at all times. This can allow or be used to acquire more than one point that is the same position with both of the tracking devices 70a and 70b. This can assist in registration of the EP tracking system 22 and the EM tracking system 24. It will be understood, however, that the two tracking devices 70a and 70b need not be the same device to acquire more than one point that is at the same position with both of the tracking devices 70a and 70b.

Even when the two tracking devices 70a, 70b are the same device or formed to be at the same or fixed relative positions, a third tracking device can be provided. For example, the tip electrode 92 can also be interconnected with the controller 72. Thus, the position of the tip electrode 92 can be tracked once it has exited the catheter 122.

In addition, or alternatively, it will be understood that the EP tracking device 70a and the EM tracking device 70b need not be positioned on top of one another, but can be positioned substantially at a known fixed location relative to one another or next to each other with a selected assembly. For example, an electrode of the EP tracking device 70*a* can be positioned substantially abutting coils of wire defining the EM tracking device 70*b*. They can also be positioned a distance from one another at a substantially known location, at least when a device is at a known configuration. The known relationship or relative positions of the EP tracking device 70*a* and the EM tracking device 70*b* can be used to register the EP tracking system 22 and the EM tracking system 24 even if the EP tracking device 70*a* and the EM tracking device 70*b* are not at the same location.

Turning to FIG. 8, navigating the EP tracking device 70*a* in block 140 is described in further detail. Movement of the EP tracking device 70*a* can be determined in block 200. The movements of the EP tracking device 70*a* can then be registered to the coordinates of the EM tracking system 24 in block 202. As discussed above, registration of the EP tracking system 22 and the EM tracking system 24 allow for a registration of a coordinate in the EM tracking system 24 with a determined position of the EP tracking device 70*a* in the EP tracking system 22.

Because of the registration of the EP tracking system 22 and the EM tracking system 24, a position of the EP tracking device 70*a* can be illustrated or displayed on the display device 38, 40 in block 204. As discussed above regarding FIG. 6, a tracked position of just the EP tracking device 70*a* with the EP tracking system 22 can be displayed on the display device 40 relative to the image data 80. For example, the icon 70*ai* representing a position of the instrument tracked with the EP tracking device 70*a* can be displayed on the image data 80.

Merging preoperative acquired image data, such as the image data 80, can be done to intraoperative acquired image data in block 206. The merging of the image data can occur in any appropriate manner. One appropriate method can include contour merging, which matches contours in the preoperative acquired image data and intraoperative acquired image data. For example, if image data of a vertebra is acquired preoperatively and contours of a vertebra is acquired intraoperatively they can be matched. The contours can be manually or automatically determined in the image data and matched between image data sets.

Additionally, tracking the EP tracking device 70*a* can be used to create point clouds for various organs. For example, a point cloud or point cloud map can be generated for a portion of the heart 84. The point cloud can then be matched, such as with contour matching or landmark matching, with preoperative acquired image data. Point cloud matching or generation includes identifying one or more points with the tracking device 70, such as with the EP tracking device 70*a* to generate a surface of a volume. Appropriate cloud mapping techniques include those described in U.S. patent application Ser. No. 12/117,537, filed on May 8, 2008, incorporated herein by reference. It will be understood, however, that the generation of the point cloud can be made with either the EP tracking device 70*a* or the EM tracking device 70*b*. However, the EP tracking device 70*a*, which can include an electrode, can be provided at a selected size, such as one that will easily maneuver within the heart 84 to allow for an efficient generation of the cloud map by identifying a plurality of points. Accordingly, a selected one of the tracking devices 70*a*, 70*b* can be efficiently used to generate a selected type of data, such as a landmark or cloud map, for merging of intraoperative and preoperative image data.

In addition, the electrode 92 of the lead 90 can be used as the EP tracking device 70*a*. The tip electrode 92 can be implanted in the heart 84. Accordingly, image data 80, which can be pre- or intra-operatively acquired, can be used to identify or suggest a selected location of the lead tip 92. By registering the EM tracking system 24 and the EP tracking system 22 a selected location identified relative to the image data 80 can be used to guide the electrode 92 to an appropriate or selected location for implantation. An additional tracking device, such as the EM tracking device 70*b*, is not required to track the electrode 92 to a selected location within the heart 84 with the image data 80 because of the registration of the EM tracking system 24 and the EP tracking system 22. Suggesting a placement of a lead tip can be based on any appropriate information, such as historical data, statistical data, or atlas models. Exemplary suggestion systems include those disclosed in U.S. Patent Application Publication No. 2002/0097806, published on May 20, 2004, incorporated herein by reference.

As discussed above, the EM tracking system 24 and the EP tracking system 22 can be used for different tracking purposes or in different locations. In addition, the EP tracking system 22 may not generate an appropriate signal in various portions of the patient 36. For example, if the EP tracking device 70*a* is not positioned within a portion of the patient 36 that includes an electrolyte or appropriately conducted material, a voltage may not be generated relative to the EP tracking device 70*a* when a current is induced in the patient 36. Therefore, the EM tracking device 70*b* can be used to track the position of the instrument 26 relative to the patient 36.

According to various embodiments, the EP tracking device 70*a* can be substantially smaller than the EM tracking device 70*b*. For example, the EP tracking device 70*a* may only include a single wire or small conductive member to act as an electrode, and, thus have small dimensions. The small dimensions of the electrode of the EP tracking device 70*a* can allow it to move to selected locations, such as within the heart 84, which may not be accessible with a larger tracking device, such as the EM tracking device 70*b*. Therefore, providing the EP Tracking system 22 and the EM tracking system 24 can allow for tracking the surgical device 26, or any appropriate device, with more than one modality.

The EP tracking system 22 can be used to track the lead electrode 90 as the EP tracking device 70*a*. Accordingly, the EP tracking system 22 can be used to track the location of the lead electrode 90 to its intended implantation site or location with the EP tracking device 70*a*. The tracked position can then be displayed on the display devices 38, 40 for viewing by the surgeon 34.

The EP tracking system 22, however, may not be directly registerable to the image data 80. As discussed above, varying impedances of tissue of the patient 36 may inhibit registration of the EP tracking system 22 with the image data 80. Lack of registration with the image data 80 can reduce effectiveness of image navigation.

The EM tracking system 24, however, can be registered with the image data 80. The EM tracking system 24, including the more uniform navigation domain, can be registered to the image data 80. In determining one or more points, also referred to as identity points, in both the EP tracking system 22 navigation domain and the EM tracking system 24 navigation domain the two tracking systems can be registered. This can allow the EP tracking system 22 to be registered to the image data 80. Registration can also allow the use of pre-acquired image data that can be registered to intraoperative image data or other appropriate image data for navigation of the instrument 26 with the EP tracking device 70*a*.

In addition, the two tracking systems 22, 24 can be used for complementary purposes. For example, the EM tracking system 24 may have a higher accuracy than the EP tracking system 22. Therefore the EM tracking system 24 can be used to determine locations of various landmarks for registration, while the EP tracking system 22 is used for navigation of the instrument 26 for implantation. Also, if location and size permits, the EM tracking system 24 can be used to confirm a location of the instrument 26 after implantation.

Further, the EM tracking system 24 can track the tracking device 70b in the absence of a conductive material. Thus, the EP tracking device 70a can be used to track the instrument when a conductive medium and current is present (e.g. within the heart 84) and the EM tracking device 70b can be used to track the instrument 26 when the conductive medium is not present. For example, if a catheter were placed in or made to traverse a volume surrounded by air, such as the windpipe or puncture a lung and get in an air sac, the EP tracking system 22 may not be able to track the EP tracking device 70a.

The flow chart 130 illustrating the method for registering or coordinating dual or two tracking system types illustrates a general overview of a registration, also referred to as a corresponding, method. It will be understood, however, that the registration of two tracking systems can be performed according to any appropriate method. For example, as illustrated in FIG. 9, a flow chart 250 illustrates a method of registering the coordinates of the EP tracking system 22 and the EM tracking system 24. The EP tracking system 22 can generate a navigational domain by injecting a current into the patient 36 to define patient space with injection or axis electrodes. The EM tracking system 24 can generate a navigational domain in patient space with an EM localizer that generates EM fields. Registering the two tracking systems 22, 24 is understood to allow a position determined with one of the tracking systems to be corresponded or registered to or known in the coordinates of the other tracking system. This can further allow illustration of a position of a tracked instrument on registered image data.

The method according to the flowchart 250 can start in block 251 and then proceed through three main phases. In the first phase, in block 252 the EP tracking system 22 and the EM tracking system 24 are registered to one another. In the second phase, in block 270 the displacement of the EP determined physical (patient space) position relative to the EM determined physical (patient space) position of the tracked instrument is determined and saved or stored. In the third phase, in block 280 the EP position data is corrected or interpolated to illustrate or output the registered or corresponding position of the EM tracking system 24 based on the registration and the determined displacement in the first and second phases.

Phase I: Register EM Tracking System Coordinates and EP Tracking System Coordinates in Block 252.

1. Synchronize Time or Data Position Collection in Two Tracking Systems in Block 258, e.g. the EM Tracking System 24 and the EP Tracking System 22. (Step I.1.)

The EM tracking system 24 and the EP tracking system 22 should be synchronized during simultaneous position acquisition, as discussed herein. The purpose of the registration is to allow registration or correspondence between positions determined by each of the two tracking systems 22, 24. Accordingly, to properly compare simultaneous positions, the two tracking systems 22, 24 should allow for synchronous position acquisition and determination. It will be understood, however, that synchronous position acquisition need not only require the same physical position acquisition at the same instant, rather it can also include determining a time when a position is determined with one of the two tracking systems and a time when a similar, same, or related position is determined with the other tracking system.

One method for synchronization can include identifying a first pedal press of the foot pedal 54 in each position data set for each of the two tracking systems 22, 24. The pedal press can be, however, any appropriate physical input by the user 34 to each of the tracking systems to identify an initial position determination or point acquisition. The pedal press in each data set can be used to compute the time offset between the two position data sets.

In addition or alternatively to using a pedal press, other information can be used to synchronize a timestamp for the data collected. For example, the two tracking systems 22, 24 can be interconnected with a network system and the network time protocol (NTP) can be used to synchronize timestamps for the position data collection. Alternatively, or in addition thereto, any other data transmission system, such as a USB cable, can be used to synchronize or send a synchronization signal to synchronize the two tracking systems 22, 24.

In addition, a position sampling signal can be sent from one of the tracking systems, such as the EM tracking system 24, to the other of the tracking systems, such as the EP tracking system 22. The signal is to allow the acquisition of a position determination simultaneously with both tracking systems 22, 24. The position collection command can allow for inherent registration between the two tracking systems 22, 24. It will be understood, however, that latency may exist between the issuance of the command to collect the position data and the actual collection of the position data. Once the latency between the provision of the command and the collection of the position data is accounted for, the two tracking systems 22, 24 can be synchronized. It will be understood, however, that the position determination instruction can be issued from either of the tracking systems, such as from the EP tracking system 22 to the EM tracking system 24 or vice versa.

A single signal, whether a pedal press or otherwise can synchronize the timing of the two tracking systems. Position data can be acquired and time stamped. The time stamped data can then be compared, beginning at the synchronous event, for the registration of the multiple tracking systems.

Additional synchronization techniques can include motion detection and analysis. For example, the position data collected with both of the tracking systems 22, 24 can be used to determine motion of the respective tracking devices in each of the tracking systems 22, 24. The position data can be used to determine the motion of the respective tracking devices. The respective sensors are moved within the volume of the subject, such as the patient 36. When the respective tracking devices or position elements are positioned within the patient 36, such as within the heart 80, motion can be induced and position can be changed in the respective tracking devices due to respiration, blood flow, movement of the heart, or movement of the catheter. Particularly if motion is quite vigorous, for example, when the position elements are positioned near the right ventricle or apex, a great deal of motion can be determined. The same or similar determined motion can be used to relate or determine similar positions of two tracking devices.

The sampling rate for the tracking systems 22, 24 can be relatively high compared to the motion within the patient 36. For example, a heart beat can be on the order of one half to one second while a sampling rate can be at least about ten per second. Accordingly, a plurality of samples can be collected for each heart beat. Thus, a relatively great deal of motion data can be collected and analyzed or compared between the two tracking systems 22, 24 to achieve an accurate synchronization signal.

Regardless, a plurality of position samples can be analyzed for determining motion of the respective position elements. It will be understood that the analysis can be used to synchronize all of the data or certain portions of the data using an analysis over time of the motion. The data can be synchronized by determining when in time the motion is substantially identical to synchronize the collected position data.

Once the data is synchronized, a coordination or registration between the two tracking systems 22, 24 can be completed as discussed herein. The registration can be based upon the acquisition of the position data with one or both of the tracking systems and determining a look up table for a relationship between the EM and EP tracking systems 22, 24. Once an appropriate transformation is determined, as discussed further herein, and a look up table or other appropriate system is defined, a translation can be made between a position determined with either of the tracking systems 22, 24 and translated to the coordinate system of the other of the two tracking systems 22, 24.

Part 2. Collect Position Data with Both the EP Tracking System 22 and the EM Tracking System 24 in Block 260. (Step I.2.)

Once the position collection is synchronized between the EM tracking system 24 and the EP tracking system 22, a plurality of position data samples can be collected. For example, 10, 50, 200, or any appropriate number of position data samples can be collected. It will be understood, that the position data samples collected, starting with the first synchronized data sample, can be collected with synchronization, such as with one of the two tracking systems providing a data collection signal, or synchronizing the two data sets, such as with motion analysis. Accordingly, it will be understood that the data sample used for the translation or coordination between the two tracking systems 22, 24 can be data that is collected after synchronization has occurred between the two tracking systems 22, 24 or after a plurality of data from both of the two tracking systems 22, 24 have been synchronized. However, the position data can be collected and analyzed with the synchronous information as opposed to both tracking systems synchronously collecting position data.

It will be further understood that any appropriate number of substantially synchronized data points can be collected or used for translation between the two tracking systems 22, 24. A linear interpolation can be made between the two nearest points in both of the EM tracking system position data and the EP tracking system position data to generate pairs of synchronized or substantially synchronized position data. As a further example, if the position data are collected after a synchronization, such that the data is not previously collected and a synchronization is determined after the collection, an interpolation can be made between the two nearest points generated in each of the two tracking systems 22, 24. Accordingly, any appropriate number of synchronized position data points can be collected or used between the two tracking systems 22, 24.

Part 3. Determining a Transformation Between the EM Tracking System 24 and the EP Tracking System 22 in Block 262. (Step I.3.)

A transformation can be made between the EM tracking system 24 and the EP tracking system 22, as discussed herein. The transformation can be between the EM tracking system 24 and the EP tracking system 22 based upon the pairs of synchronized points obtained, as discussed above. It will be understood that position data points from the EP tracking system 22 can be translated into the EM tracking system 24 coordinate position data and vice versa. The discussion herein regarding transforming the EM position data to the EP tracking system 22 coordinate system is merely exemplary.

A non-linear optimization procedure can be used to find an Affine transformation between each of the pairs of points from the two tracking systems 22, 24. For the following discussion a position data point from the EP tracking system 22 can be referred to as 22p and a position data point from the EM tracking system 24 can be referred to as 24p, as illustrated in FIG. 9A. The transformation can minimize the sum of the square of distances between the EP points 22p and the EM points 24p that are related in time to each other. That is, that points that are compared were collected at the same time or at the same physical location due to the synchronization. Appropriate optimization methods can include the Nelder-Mead method, such as that described in Nelder, J. A. and Mead, R. "A Simplex Method for Function Minimization." *Comput. J.* 7, 308-313, 1965. With two tracking systems 22, 24 operating independently, position data points may not be collected at the same time. Therefore, the navigation system 20 can interpolate position and time samples. The interpolation can include determine a difference in time or the time when a position data point in each of the two tracking systems was collected at different times for the same physical location.

The two points should be at the same physical position when an appropriate and calibrated instrument is used, as discussed herein. Briefly, according to various embodiments, a single instrument can have a first tracking device tracked with the first tracking system 22 and a second tracking device tracked by the second tracking system 24 at substantially the same physical (e.g. patient space) position.

The affine transformation can include several parameters for the transformation of the EP position data to the EM position data, for example 10 parameters. The parameters can include translating each of the EM points 24p to center on the origin. Translating the EM points to center on the origin can include three parameters, at least, because the position points exist in three dimensional space along three axes, as discussed above. Accordingly, each of the EM points will have three dimensions each relating to one of the three parameters to translate the EM points to center on the origin.

The EM points 24p can also be uniformly scaled with at least one parameter to enlarge the cloud or volume of the EM points. As discussed above, the EM and EP tracking systems 22, 24 can be used to generate a plurality of points to identify a surface, such as an internal surface of a heart of the patient 36. Accordingly, both the EM and EP tracking systems 22, 24 generate a plurality of points that are used to identify or generate a surface.

Three parameters further are to rotate the EM points 24p around each of the three axis. Rotation around each of the axis can relate to one of the three parameters. The EM tracking system 24 is not aligned to the patient, unlike the EP tracking system 22, due to the placement of the axes patches on the patient 36. The axes patches on the patient 36 do the alignment of the EP tracking system 22 to the patient 36. Registration includes not only distance but coordinate alignment of the EM tracking system 24 coordinates to the EP tracking system 22 coordinates, thus rotation is necessary.

Finally, three parameters can include translating the EM points 24p to the center of the EP points 22p from the origin. The center of the EP points can be determined by identifying an outer most extent of the EP position points and determining a center related to all of the outer most points. It will be understood that any other appropriate center or identification of a position within the EP points 22p can be determined and translating the EM points 24p to the center or other determined point can be made along each of the three axis to determine or generate the three final parameters. The ten parameters, as discussed above, can be optimized using the appropriate optimization algorithm or method, such as the Nelder-Mead optimization method.

Part 4. Transform the EM Points 24p in Block 264 with the Determined (e.g. Affine) Transformation Optimized in Block 262 (Step I.4.)

Once the affine transformation has been optimized, it can be applied to the EM points 24p. In transforming the EM points 24p, the EM points 24p and the EP points 22p should include substantially identical positions in generated space. In other words, when displayed on the display device, the surface or cloud of position data points collected with both of the EM tracking system 24 and the EP tracking system 22 should appear to be substantially identical. The transformation, therefore, can be used to coordinate or register the coordinate systems of the EP tracking system 22 and the EM tracking system 24. Once registered a position data point determined with one of the tracking systems can be registered to the other tracking system. As discussed above, this can allow for the EP position data point 22p to be superimposed on image data based on a registration of the EM tracking system 24 to appropriate image data (such as external image data including magnetic resonance image data).

In addition, it will be understood, that the transformation can also be to transform the EP position data points 22p to the EM coordinate system. As discussed above, the EM coordinate system is substantially uniform and generally can be related more strictly to three dimensional coordinates of the patient 36.

Phase II: Determine Local Displacements Between the EM Tracking System and the EP Taking System in Block 270

Part 1. Sample or Collect Additional Positions to Generate Additional Position Data Points in Block 272. (Step II.1)

After the transformation has been determined between the EM data points 24p and the EP data points 22p, as discussed above, additional position data points can be collected with the EP tracking system 22 and/or the EM tracking system 24. Generally, position data points can be collected at any appropriate rate or frequency for generation of a map of a volume, which can be rendered as a surface or a plurality of points or managed points, as discussed above. The frequency of data collection can be any appropriate frequency, such as about a position data point every one second or about twelve times per second.

Because the transformation has been determined, as discussed above in Step I.4, each of the data points collected in either of the two tracking systems 22, 24 can be substantially instantaneously or continuously transformed to the coordinate system of the other tracking system. For example, if the EP tracking system 22 is used to collect additional position data points, then the navigation system 20, or a processor thereof executing instructions, can transform the additional EP position data points to the EM coordinate system.

Any appropriate amount of position data can be collected and used to generate a map, as discussed above. Further, the transformation can be between any two appropriate navigation or tracking systems rather than just between an EM and EP tracking system.

Part 2. Determine and Store a Vector From Each EP Point 22p to a Synchronized and Corresponding EM Point 24p of the Two Tracking Systems 22, 24 in Block 274. (Step II.2.)

As each position data point is collected, for example with the EP tracking system 22, a vector 22v (FIG. 9A) can be computed between each of the actually collected EP position data points 22p and the corresponding EM position data point 24p. The vector from the EP position data point 22p to the corresponding EM data point 24p can be based upon the transformation discussed above. The vector 22v between the EP and EM points 22p, 24p can be stored and saved in an octree for each of the EP position points 22p collected.

As is understood by one skilled in the art, an octree is a spatial data structure that can be used to map points and space to data. In this instance, the data can include the vector 22v from each of the EP points 22p to the EM points 24p and the spatial information can be related to the spatial position of the EP point 22p and the position data relating to that point. Accordingly, for each of the position data points that are collected including the EP position data points 22p, a vector 22v can be determined to a corresponding EM data point 24p and stored in an appropriate data structure for later access.

Part 3. Create a Three Dimensional (3D) Look-Up Table in Block 276. (Step II.3.)

Once the vector has been determined and stored, as discussed above in Step II.2. a three dimensional or appropriate look-up table (3D-LUT) can be generated or created. The three dimensional look up table can include a plurality of grid points in three dimensional space. For each of the points in the look up table, an average of each of the vectors between the EP and EM points can be determined within a given radius from the respective grid points. The vectors that are stored in the octree, discussed above, can be efficiently accessed within the given radius from the selected grid point to generate the look up table.

The grid points within the three dimensional space can be related to the information in the 3D-LUT. Accordingly, information regarding each of the points within a respective grid can be stored in the 3D-LUT. It will be further understood that the grid points can be positioned at any appropriate density or spacing for use in 3D-LUT.

Phase III: Correct The EP Position Data in Sub-Routine Block 280.

Part 1. Linearly Interpolate EP Position Data Points in Block 282. (Step III.1.)

Once the 3D-LUT has been created in Step II.3. the data can be interpolated or corrected in Phase III. In particular, according to the example discussed in particular here, each of the EP position data points can be corrected or interpolated to the EM coordinate system of the EM tracking system 24. Initially, the EP position data points can be a linearly interpolated to relate to the EM coordinate system. The 3D LUT generated in Step II.3. can include the EP position data points collected or determined with the EP tracking system 22.

The linear interpolation can be any appropriate linear interpolation and can generally include averaging the eight cells nearest the selected cell in the 3D LUT. The linear interpolation can interpolate each of the EP position data points based upon the closest eight cells in the 3D LUT generated in Step II.3. The linear interpolation will result in the determination of an interpolated displacement of each of the EP position points because the 3D LUT includes data relating to the vectors between each of the EP and the corresponding EM data points. The eight nearest cells can be the cells touching the related EP position data point cell in the 3D LUT.

Part 2. Add the Interpolated Displacement to the Determined EP Position Data Point to Determine an Interpolated EP Position Data Point in Block 284. (Step III.2.)

Following the linear interpolation of the respective cells in Step III.1, the interpolated displacement can be added to the EP position data 22p to generate an EP interpolated position data point. The EP position data point can be the data point that is collected or determined solely with the information collected with the EP tracking system 22. According to various examples, the EP tracking system 22 collects or determines the EP data point 22p with an electrode positioned within the patient 36. When only the map generated with the EP tracking system 22 is selected, the relative relation of the EP position data points to any other coordinate system is generally unimportant. When additional coordinates are selected to be viewed, however, the interpolated EP position data point can be used to relate each of the collected EP position data points to the coordinate system of the EM tracking system 24. This can allow the interpolation to be used to view a map or display of EP position points relative to other acquired image data or other fixed coordinate systems relative to the patient 36 based on the regular coordinates of the EM tracking system 24.

The interpolated EP position data point can be used to, optionally, relate to an external or a uniform coordinate system in block 290. For example, as discussed above, the EM tracking system 24 can be registered to image data of the patient 36. Accordingly, the interpolated EP position data generated or determined in Step III.2. can also be registered or related to the image data of the patient 36. Accordingly, even if the coordinate system of the EP tracking system 22 is not strictly uniform or inherently registerable to any external coordinate system, interpolation of the EP position data to the coordinate system of the EM tracking system 24 can allow for an interpolation of the coordinate system of the EP tracking system 22 to a more uniform coordinate system.

The method 250 can then end in block 292. The method in flowchart 250 can generate EP position data 22p that relates to a fixed or Euclidean coordinate system. This can allow EP position 22p data to be registered to other acquired image data through registration with the EM tracking system 24 that is registered to the other image data.

Further, the method in flowchart 250 can be used to register the coordinate system of any two tracking systems for use in any appropriate volume. Also, the tracking systems 22, 24 can be used to track any appropriate device relative to any appropriate volume. Positioning a device within an enclosed volume may be selected for building, manufacturing, or repairing various workpieces in selected workspaces. For example, a device can be moved relative to an enclosed volume, such as within an airplane, robot, or other enclosed areas, without requiring open visualization or access within the volume. The enclosed volume of the workpiece or workspace, may also include more than one type of environment. Accordingly, having multiple tracking systems using differing tracking modalities can be used to track a single instrument or two parts of the single instrument within any appropriate volume.

Instruments

According to various embodiments, a single instrument 300 for use with both the EM and EP tracking systems 22, 24 is illustrated in FIG. 10, The single instrument 300 can be based on known appropriate instruments, such as the pacemaker lead model 4074 sold by Medtronic, Inc., having a place of business in Minneapolis, Minn. The model 4074 can include a passive mounting system or tines that can be removed to allow for a substantially smooth exterior. The instrument 300 can have an exterior diameter of about 0.075 inches and have an external distal electrode 302 that can be used as the EP tracking device. Therefore, the external electrode or EP tracking device 302 can be used with the EP tracking system 22, as discussed above.

Positioned proximally, or nearer an origination point of the instrument 300 can be a coil, such as a coil of wires 304 that can be used as an EM tracking device. The EM tracking device 304 can include one or more coils of single or individual wires. For example, two coils of wires can be positioned to have axes at an angle relative to one another to obtain multiple degrees of freedom information regarding location.

A center 304c of the EM tracking device or coil of wires 304 can be positioned at a selected distance 306 from a center 302c of the EP tracking device 302. Generally, the distance 306 can be the distance between the center points of the two tracking devices 303, 304. The distance 306 between the EP tracking device 302 and the EM tracking device 304 can be known and used in the interpolation of the EM position data and EM position data, as discussed above.

The EM tracking device 304 can be fixed at the distance 306 from the EP tracking device 302 by any appropriate mechanism. For example, the EM tracking device 304 can be positioned on a tube 308 that is fixed to an exterior of the instrument 300 at the fixed distance 306 from the EP tracking device 302. The fixation of the tube 308 can be with adhesives, welding, or any appropriate fixation mechanism. Further, it will be understood, that the EM tracking device 304 can be formed as a coil of wire that is directly on the exterior of the instrument 300 as long as the EM tracking device 304 and its conductors and are insulated from other conductors of the instrument 300. If modifying an existing instrument wires or conductors 310 can be used to interconnect the EM tracking device 304 with the EM tracking system 24. An appropriate shrink wrap or insulation 312 can be provided to hold the conductors 310 and insulate the conductors 310 from the patient 36.

Accordingly, the instrument 300 that has the EP tracking device 302 and the EM tracking device 304 at the fixed distance 306 from one another can be used for acquiring EP position points and EM position points. Further, the EP positions determined with the EP tracking device 302 and the EM positions determined with the EM tracking device 304 can be determined substantially simultaneously with the single instrument 300. The navigation system 20 can use the simultaneous or substantially simultaneous measurements of position of both the EM and EP tracking devices 304, 302 to determine a registration between the two tracking systems, as discussed above and herein. Thus, the instrument 300 can be used with the two tracking systems 22, 24 to register the two tracking systems or can be used with only one of the tracking systems for determining a position of the instrument 300 within the patient 36.

As discussed above, the orientation of the EM tracking device, can be determined. The orientation of the instrument 300 can be determined with the EP tracking system 24 by determining the location of two EP tracking devices on the same instrument 300. For example, returning reference to FIG. 10, a second EP tracking device 303 can be included near the first EP tracking device 302.

The first EP tracking device 302 and the second EP tracking device 303 can both be tracked simultaneously to determine an orientation of the distal end of the instrument 300. For example, during a detection or navigating cycle, the position of both the first EP tracking device 302 and the second EP tracking device 303 can be determined. By determining the position of both the EP tracking devices 302, 303 an orientation of the instrument 300 can be determined. A line or vector can be determined between the position of the second tracking device 303 and the first EP tracking device 302. The vector can be determined by the navigation system 20, the EP tracking system 22, or by a user viewing the display 40 that can include an icon illustrating the position of both of the EP tracking devices 302, 303. According to various embodiments, the tracking system 22 can be used to determine a vector between the two EP tracking devices 302, 303.

Accordingly, an orientation of the instrument 300 can be determined with the EP tracking system 22.

With reference to FIG. 11, an instrument 340 is illustrated. The instrument 340 can be any appropriate cannulated instrument that forms an internal cannula or bore 342 within an internal structure 344. Positioned through the cannula 342 is a guide wire or stylet 346. The stylet 346 can be formed of a conductive material, such as a biocompatible metal or metal alloy or other conductive material. The stylet 346 can extend from an end 350 of the internal structure 344 to be used as an electrode or EP tracking device 348.

The stylet 346 can be a non-rigid structure such that it is able to move or deflect due to blood flow, encounters with the anatomy of the patient 36 or other solid structures. Accordingly, the EP tracking device 348 can deflect or move to deflected positions 348' relative to the end 350 of the instrument 340. The EP tracking device 348 can be moved relative to the internal structure 344 to limit or increase the amount of deflection of the EP tracking device portion 348 of the guide wire or stylet 346. Nevertheless, the EP tracking device 348 can be at a substantially fixed position relative to a coil or EM tracking device 360.

The EM tracking device 360 can be a coil, such as a coil discussed above, for use with the EM tracking system 24. The EM tracking device 360 can be formed around the stylet 346, such as a stylet provided with implantable leads sold by Medtronic Inc., having a place of business in Minnesota, USA. The EM tracking device 360 can be fixed on the stylet 346 relative to the EP tracking device 348. The EM tracking device 360 can be used to determine positions with the EM tracking system 24 substantially simultaneously with the EP tracking device 348, as discussed above.

The instrument 340 can further include a balloon or inflatable portion 366. The inflatable portion or balloon 366 can be similar to the balloon or inflatable portion of the Medtronic Attain 6215 venogram balloon instrument sold by Medtronic, Inc., having a place of business in Minnesota, USA. The instrument 340 can include the balloon to assist in movement of the instrument 340 relative to the patient 36 and assist in minimizing the possibility of a perforation. The balloon 366 can also limit the amount or depth of the EP tracking device 348 can enter into a tissue structure. The balloon 366 can also assist in moving the instrument 340 through the patient 36 by allowing or causing drag on the balloon 366 through the patient 36.

With reference to FIG. 12, schematic illustrations of instruments 370 and 380 illustrate information that can be collected or known by the navigation system 20 for determining the simultaneous or corresponding positions within the EM and EP tracking systems 24, 22. With reference to the schematic instrument 370, an EP tracking device 372 having a center 372c is positioned at a known or measured position or distance 374 from an EM tracking device 376 having a center 376c. The measured position of the EP tracking device 372 and the EM tracking device 376 can generally be the center of the respective tracking devices 372c, 376c. The distance 374 between the EM tracking device 376 and the EP tracking device 372 can be fixed and known prior to the use of the instrument schematically illustrated at 370 or it can be measured within the navigation system 20. Nevertheless, the distance 374 between the two tracking devices 372, 376 can be used in the registration between the EP and EM tracking systems 22, 24.

With reference to the schematic illustration 380, the EP tracking device 372 can be used to substantially define a single three dimensional point within the navigation volume of the EP tracking system 22. The EM tracking device 376 can also be used to define a three dimensional position and an orientation within the navigation domain or volume of the EM tracking system 24. An angle 382 can be defined between the point determined with the EP tracking device 372 and the EM tracking device 376. The angle 382 can also be inputted into the navigational system 20 or measured within the navigation system 20 to increase accuracy when determining the position of the EM tracking device 376 relative to the EP tracking device 372. The angle 382 can change depending upon the configuration of the tracking instruments or mapping instruments. For example, the EM tracking device 360 on the stylet 346 may move relative to the EP tracking device 348. Accordingly, the orientation or angle 382 between the EM tracking device 376 and the EM tracking device 372 can be determined while making measurements or determining positions of both the EP and EM tracking devices 372, 376. The orientation of the EM tracking device can also be used to confirm location of the instrument when the orientation is known relative to the EP tracking device.

Procedures

Various instruments that can be used to map or track within the tracking systems 22, 24 can also be used for various procedures. For example, the instrument 300 can also be used for ablation. The EP tracking device 302 can be configured to also provide an ablation to selected portions of the anatomy. Instruments used for ablation or lead placement can include an electrode which can be connected with the EP tracking system 22. The EP tracking system can be used to track the ablation or the implantable lead electrode. The EP tracking system 24, therefore, can be used to precisely illustrate and determine the location of the ablation electrode or the electrode for implantation.

Figure 13:
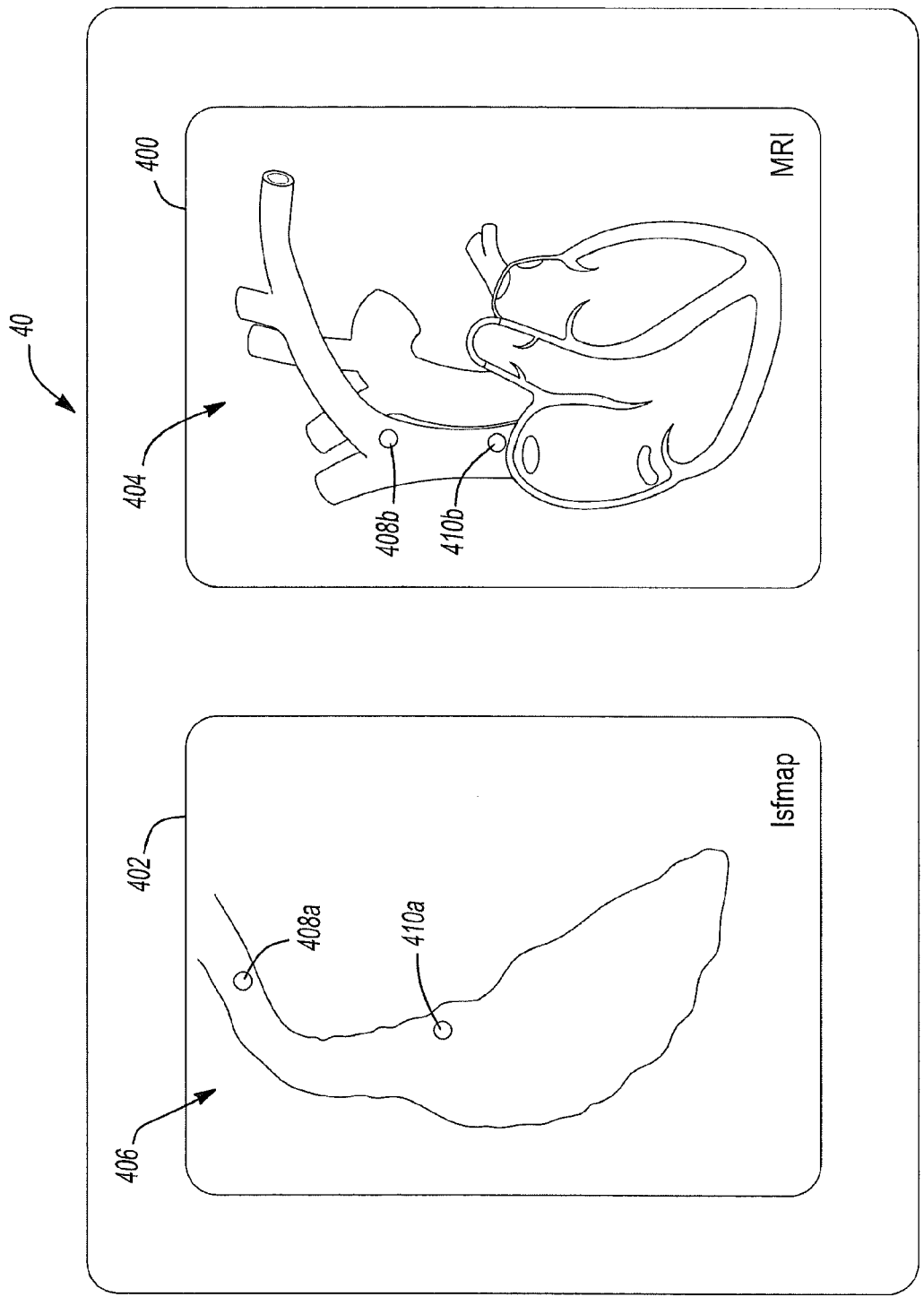
FIG. 13 is an illustration of a display device illustrating two types of image data.

With reference to FIG. 13, the display 40 can display an image that can include preacquired image data, such as from a CT or fluoroscopic scanner, in a first screen portion 400 and map image data in a second screen portion 402. As discussed above, the acquired image data can include image data, such as a CT scan image data 404. The CT image data 404 can be image data that is acquired of the patient 36 either during or prior to a surgical procedure. The map data can include EP or EM map data 406. As also discussed above, a translation between the map data 406 and the acquired image data 404 can be made based on the interpolation of the EP tracking system 22 and the EM tracking system 24. Accordingly, when an instrument is tracked with the EP tracking system 22, after the translation, a position on the instrument can be illustrated relative to the acquired image data 404 by using the EP tracking system 22 and the translation made, as discussed above in flowchart 250.

An instrument that includes an electrode, such as an ablation catheter can be tracked with the EP tracking system 22 without requiring additional tracking instrumentation associated with the tracked instrument. A first icon 408a can be illustrated on the EP map data and the second icon 408b can be illustrated on the acquired data 404 to illustrate a location of an ablation instrument relative to an anatomy of the patient 36, such as the heart 80 of the patient. In addition, the tracked location of the ablation instrument can be used to illustrate the ablation location on the patient 36 or in the heart 80.

Illustrating ablated tissue can be done by tracking the electrode used for ablation with the EP tracking system 22. Either with a manual triggering or with an automatic triggering, the navigation system 20 can be used for identifying one or a plurality of locations of ablation. For example, the ablation instrument can be tracked with the EP tracking system 22 and a location can be illustrated on the EP map data as an ablation or ablated location 410a. Due to the registration with the acquired image data 404, an ablation location 410b can also be illustrated relative to the acquired image data 404. Illustrating an ablation location relative to the image data 404 can be useful in ensuring that an appropriate ablation has occurred relative to the heart 80 or any other appropriate location. It will be understood that according to various embodiments, different ablation instruments can ablate a portion of the heart 80, or any other appropriate anatomical portion, in a point manner, linear manner, or any other type of ablation configuration. Nevertheless, due to the ability to track the location of the electrode performing the ablation, the position of the ablated tissue can be illustrated on the image data 404 acquired of the patient 36.

By illustrating the location of the ablation relative to the anatomy of the patient 36, a determination can be made as to whether further ablation may be useful in a selected patient or if an appropriate ablation has occurred. For example, it can be selected to view an ablated region to ensure an appropriate annular ablation has occurred to limit electrical pathways through the heart 80 of the patient 36. Again, by tracking the position of the electrode performing the ablation additional tracking elements may not be necessary. Thus, the EP tracking device, according to various embodiments, can also be used for ablation or other appropriate purposes.

Figure 14:
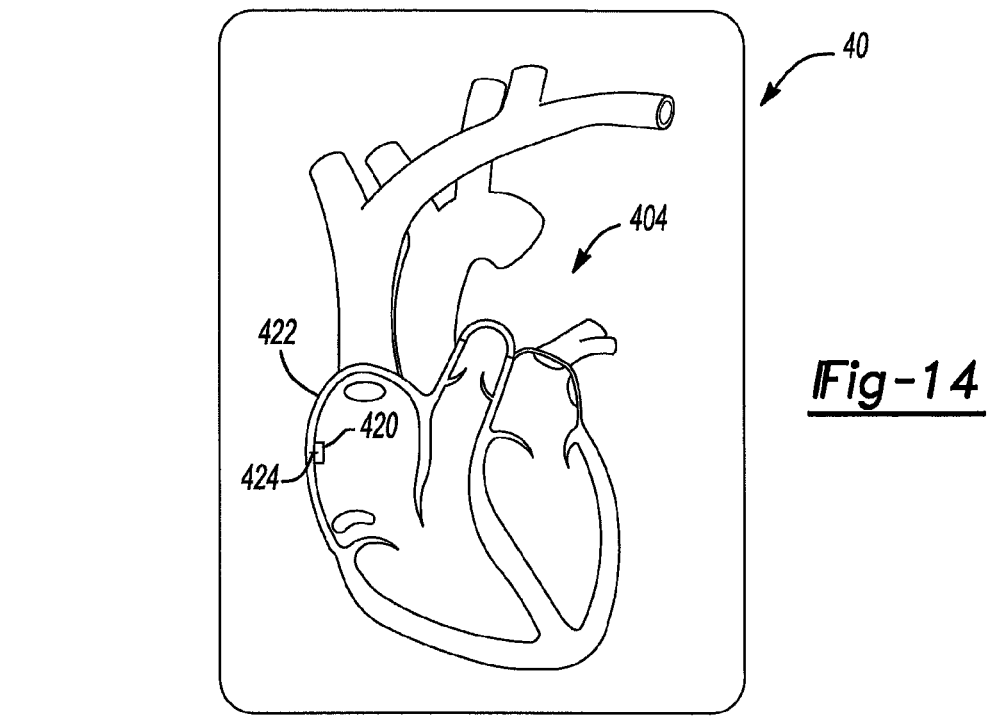
FIG. 14 is an illustration of image data with icons illustrating a location of an instrument with two tracking systems.

Similarly, the two tracking systems 22, 24 can be used simultaneously or serially for different procedures. As discussed above, after registration between the two tracking systems 22, 24, the acquired image data 404 of the patient 36 can be illustrated and a tracked position of the instrument using the EP tracking system 22 alone can be illustrated relative to the acquired image data 404. Accordingly, with reference to FIG. 14, the acquired image data 404 can be illustrated on the display 40 alone or with the position of an instrument that is tracked solely with the EP tracking system 22. An instrument, such as any appropriate instrument illustrated above, can then be navigated in the heart 80 of the patient 36 and the position of the instrument can be illustrated on the display 40, such as with an icon 420.

A portion of the instrument can then be tracked into the tissue of the patient 36, such as a wall of the heart 80 with the EP tracking system 22 alone. For example, a needle that is conductive can be tracked into a wall 422 of the heart 80. A position of the needle can be illustrated as a second icon 424 pushed into the wall 422. An infarct in the heart 80 can be treated with selected treatment, such as the injection of proteins or growth factors. Knowing the position of the needle within the heart wall 422 can assist in ensuring an appropriate positioning of the needle during injection of the selected treatment. Accordingly, as the needle is pushed into the wall 422 of the heart 80 it can be tracked with the EP tracking system 22 and its position illustrated relative to the acquired image data 404 of the patient 36 due to the translation between the EP tracking system 22 and the EM tracking system 24. The EM tracking system 24 can be registered to the image data 404 and the EP tracking system 24 can also be also be registered to the image data, or co-registered to the image data, due to the registration with the EM tracking system 24.

As illustrated here, and discussed above, the registration between the EM tracking system 24 and the EP tracking system 22 allows the position of the EP tracking device, according to various embodiments, to be illustrated as if it is being tracked with the EM tracking system 24. The registration of the EP tracking system 22 with the EM tracking system 24 allows for the tracked position of the EP tracking device to be illustrated relative to the acquired image data 404 as if it were being tracked with the EM tracking system 24.

Tracking System Variations

According to various embodiments, the EP tracking system 22 is used to inject a current into the patient 36 through the various axis patch pairs 60a-64b. The axis patch pairs can each inject a current into the patient 36 at a different frequency. The frequency injected into the patient 36, however, is generally within a range that is safe for injection into the patient 36. Accordingly, other systems may inject a current or use a current of a frequency that is similar to that which can be used by the EP tracking system 22. Accordingly, the EP tracking system 22 can include a system to monitor and switch frequencies within the patient 36. The circuitry within the EP tracking system 22 can detect or measure currents from other instruments connected to or within the patient 36, at selected times. If a current is found to be within a frequency range used by the EP tracking system 22, a different frequency can be selected and switched to for injection between a selected pair of the axis patches. Such a frequency hopping or frequency agility system can include that disclosed in U.S. patent application Ser. No. 12/421,364, Filed on Apr. 9, 2009, and entitled METHOD AND APPARATUS FOR MAPPING A STRUCTURE, incorporated herein by reference.

The two tracking systems, including the EP tracking system 22 and the EM tracking system 24, can include different or alternative localizing systems. As discussed above, the axis patches 60a-64b can be used to inject axis currents within the patient 36. An EM localizer, such as the selected EM coil set, can be used to generate a navigation domain relative to the patient 36 or within the patient 36. It can be selected to position the EM localizer 76 relative to the patient 36 to substantially align the navigational domains of the EM tracking system and the EP tracking system.

For example, with reference to FIG. 4, the EM localizer 76 can be positioned over the heart 84, as illustrated in phantom 76'. Minimizing or lessening the translation between the EM tracking system 24 and the EP tracking system 22 can be achieved by positioning the EM localizer 76' over the patient 36 to substantially align an EM navigational domain axis with an axis of the EP tracking system 22. Thus, the alignment of the EP tracking system 22 and the EM tracking system 24 can be used to assist in determining the location of the tracked devices within the respective tracking system navigational domains and can assist in aligning or determining an orientation of the instruments within both of the tracking system navigational domains.

The orientation of the instrument 300 can then be translated relative to the orientation of the EM tracking device 304. Thus, when the instrument 300 is tracked with the EP tracking system 22 alone, an orientation of the instrument 300 can also be illustrated relative to the coordinate system of the EM tracking system 24. It will be understood that any appropriate instrument can be used to include two or more EP tracking devices and the instrument 300 is merely exemplary.

The EP tracking system 22 can include reference patches that are connected to the patient 36 for referencing the tracked devices or the EP points relative to reference portions of the patient 36. The reference patches can be positioned on the patient 36 at appropriate positions such as over the xiphoid of the patient 36 and substantially opposite the xyphoid on a dorsal or back of the patient 36. The reference patches can provide a rough anatomical orientation relative to the patient 36 and can also be used to re-orient the EP data if an error occurs, but at least one of the reference patches is maintained connected to the patient 36. The use of the reference patches can be used to describe in U.S. patent application Ser. No. 12/421,364, Filed on Apr. 9, 2009, and entitled METHOD AND APPARATUS FOR MAPPING A STRUCTURE, incorporated herein by reference. In addition, it will be understood that reference patches used with the EM tracking system 24 can also be used with the EP tracking system 22 and vice versa. That being, the reference patches can be used with the EM tracking system 24 as well.

Calibration Techniques

Figure 15A:
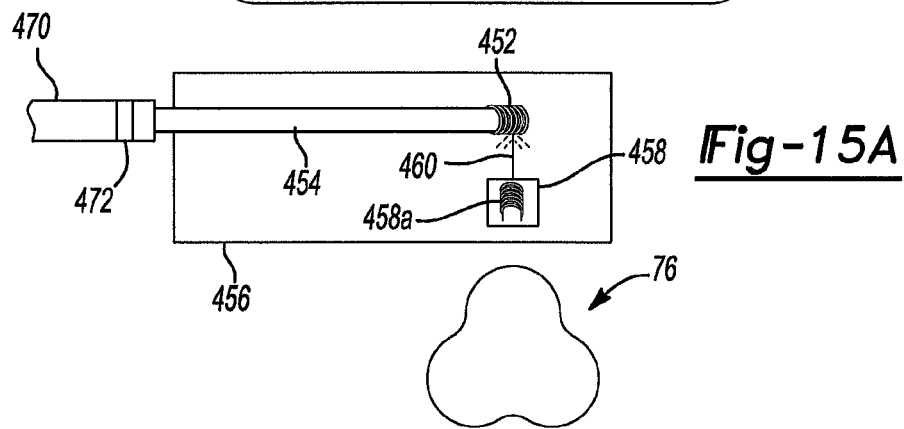
FIG. 15A is a plan view of a calibration jig with one instrument associated therewith, FIG. 15A' is a plan view of an alternative calibration jig system with one instrument associated therewith.
Figure 15A:
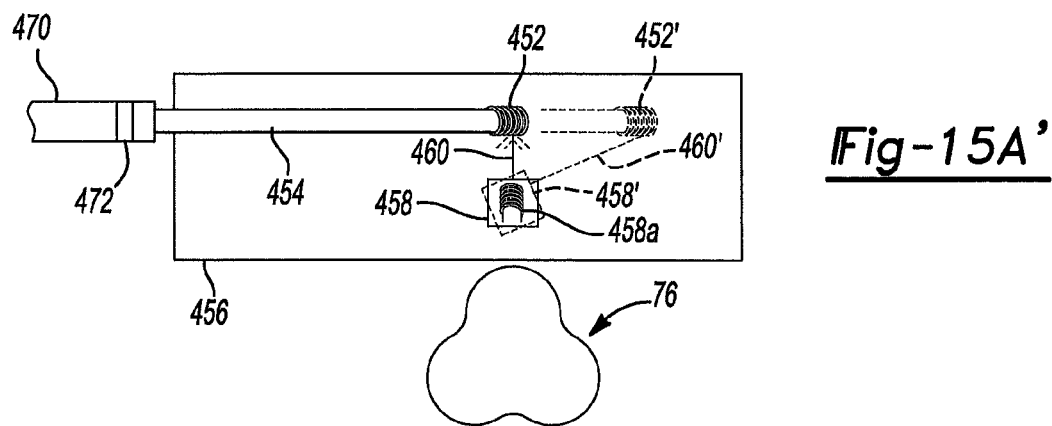

It can be selected to calibrate a location of an EM tracking device 452 relative to an EP tracking device 472. As illustrated in FIGS. 15A, 15A' and 15B, an EM tracking device 452 is connected with a guide wire or stylet 454 that is connected or otherwise associated with a fixed base of a fixture or jig 456. The fixture 456 can be positioned within the navigation domain of the EM localizer 76. The EM localizer 76, in combination with the EM tracking system 24, can determine the location of the EM tracking device 452. An external indication system can provide an indication of a location of the EM tracking device 452 or indicate when the EM tracking device has reached a selected or targeted location.

The external indication system, for example, can be a laser module 458 this is automatically powered to emit a laser light 460 at a target. It will be understood that the external indication source can emit a selected emission, such as a visible emission. The target can be the location of the EM tracking device 452. The target can be determined relative to the fixture 456 and the laser module 458 can be activated to emit the beam 460 to indicate the target when the tracking device 452 is determined to be aligned with the target. The external indication system, including the laser module 458, can move relative to the fixture base 456 to point the laser emission 460 at the target. The laser module 458 can rotate around an axis or translate linearly along an axis.

As illustrated in FIG. 15A', the laser module 458 can be automatically or mechanically moved relative to the fixture 456 to align with the target. For example, a selected linear or axial actuator can be associated with the laser module 458. Also, a laser EM tracking device 458a can be associated with the laser module 458 to track the location of the laser module 458. As discussed above, the EM tracking device 452 can be fixed at a selected location on the fixture 456 and the laser emission 460 can be pointed at a target representing the location of the EM tracking device 452. The laser module 458 can be aligned by tracking the laser module 458 with the EM tracking system 24. This can allow the EM tracking device 452 and the laser module 458 to be tracked with the same tracking system and aligned for determining the location of the EM tracking device 452 for calibration.

The laser module, or the portion of the laser module 458 that emits the laser light 460, can be mechanically moved relative to the fixture 456. By moving the laser module 458, the target to be illuminated or indicated with the laser module 458 need not be fixed relative to the fixture 456. The laser module 458 can be tracked with the EM tracking system 24 because it is also within the navigational domain generated by the EM localizer 76. Thus, the laser module 458 and the EM tracking device 452 can both be tracked at the same time with the same EM tracking system 24. Alternatively, multiple tracking systems can be used that are registered. Because both the laser module 458 and the tracking device 452 are tracked at the same time and the laser module 458 can be moved, the laser beam 460 can also be moved to illuminate or indicate the location of the target which is the EM tracking device 452.

As illustrated in FIG. 15A', the laser module 458 can be moved from a first position 458 to a second position 458'. This moves the laser light from a first position 460 to a second position 460'. The movement of the laser module 458 can be used to indicate the location of the EM tracking device 452 as it moves from a first position 452 to a second position 452'. As the laser emission 460 is pointed at the target of the EM tracking device 452 anything positioned over the EM tracking device will be illuminated by the laser emission 460.

According to various embodiments, as illustrated in FIGS. 15A and 15A' the indication module, such as a laser module 458, can be used to indicate the location of the EM tracking device 452. The EM tracking device 452 can be indicated with the laser module by illuminating or indicating a target location which can be the location of the EM tracking device 452. The target can be a fixed location, as illustrated in FIG. 15A or can be a moveable location that is tracked, such as with the EM tracking system 24, as illustrated in FIG. 15A'.

A second instrument portion 470, which includes an EP tracking device 472 can then be positioned relative to the stylet 454 including the EM tracking device 452. As illustrated in FIG. 15A, a laser light beam 460 can be directed at the location of the EM tracking device 452. The second instrument 470 need not be tracked, although it can be, because the alignment is done by viewing and confirming when the laser emission 460 illuminated the EP tracking device 472. When the EP tracking device 472 is illuminated alignment can be confirmed, as discussed below.

Figure 15B:
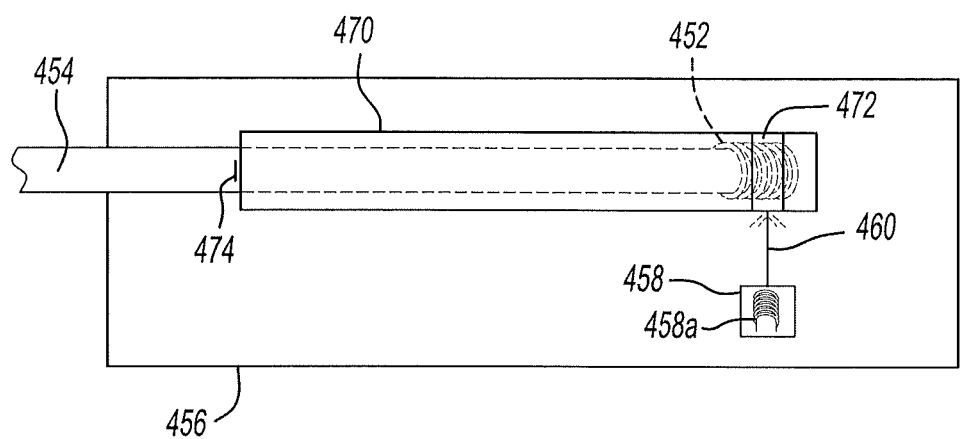
FIG. 15B is a plan view of a calibration jig with two instruments associated therewith.

With reference to FIG. 15B, the second instrument portion 470 can be slid over the stylet 454 while held relative to the fixture 456. Once the EP tracking device 472 is aligned with the laser beam 460, the system can be calibrated or instructed to indicate that the EM tracking device 452 is aligned with the EP tracking device 472. Once the laser beam 460 is used to align the EP tracking device 472 with the EM tracking device 452, the stylet 454 can be physically marked at the end of the second device 470. For example, an ink marking or other marking 474 can be used to indicate the position of the stylet 454 relative to the second instrument 470.

The stylet 454 and the second instrument 470 can then be removed from the fixture 456. The two portions of the instrument can then be inserted together or sequentially into the patient 36 to be tracked with the two tracking systems 22, 24. The marking 474 can be used to determine when the EM tracking device 452 is aligned with the EP tracking device 472. Therefore, the alignment or co-positioning of the two tracking devices 452, 472 can be made without viewing the two tracking devices and internally within the patient 36.

Further, by tracking the EM tracking device 452 any appropriate signal can be emitted by the exterior indication source when the EM tracking device reaches a target. Exemplary signals include audible signals, visual signals, tactile signals, or combinations thereof. The signals can be generated based on the tracked location of the EM tracking device and a determined location of the lead or catheter being moved relative to the fixture 456. A similar or different signal can then be emitted when the EM tracking device is aligned with the EM tracking device 452 or when it is seen to reach a market target on the base fixture 456.

Cyclic features of the patient 36 can be used to calibrate or classify the positions of the tracking devices, including the EM tracking device 452 and the EP tracking device 472. For example, the position data for each of the tracking devices can be classified within a particular respiratory or cardiac cycle of the patient 36. The differently characterized positions can be used to generate maps of the patient 36 at different portions of the cycle. The different maps can then be played in sequence or otherwise illustrated or synchronized to the patient 36. In addition, the position data that is characterized can be displayed on the display 40 for viewing by the user based upon the appropriate and detected cycle of the patient 36. For example, positions that are collected during an inspiration of the patient 36 can be displayed on the display 40 when inspiration of the patient 36 occurs. This can assist in increasing clarity and accuracy of the illustrated positions on the display 40 by accounting for movement of the patient 36 relative to the instruments within the patient having the tracking devices. Classifying the position data is further discussed in U.S. patent application Ser. No. 12/421,364, Filed on Apr. 9, 2009, and entitled METHOD AND APPARATUS FOR MAPPING A STRUCTURE, incorporated herein by reference.

Further, the translation or distance between the respective EM tracking devices and the EP tracking devices can be determined using selected external or additional image modalities. For example, fluoroscopy can be used to determine a distance between two tracking devices if both of the tracking devices are radio opaque. Although it can be selected to eliminate or substantially reduce the use of ionizing radiation during a procedure, such as may be used in fluoroscopy, fluoroscopy can be minimally used to determine certain information.

Additional imaging systems can also be used to obtain information of the patient 36 or information regarding the mapping or trackable devices. Imaging systems can include ultrasound (US), computed tomography (CT), magnetic resonance imaging (MRI), and other appropriate imaging techniques can be used. For example, an US system can be used to image or view the position of the selected tracking device within the patient 36. An US transducer can be used to view the tracked device and determine its position in the patient 36. Accordingly, selected imaging systems can be used to image the location of the instrument within the patient 36. As discussed above, this can also be used to determine a distance between two tracked devices within the patient 36, such as for translation or registration purposes between the two tracking systems 22, 24.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of correlating a first coordinate system of a first tracking system and a second coordinate system of a second tracking system, comprising:
   determining a registration of the first coordinate system of the first tracking system and the second coordinate system of the second tracking system based on determining a first position with the first tracking system and determining a second position with the second tracking system;
   determining a vector displacement between the determined first position of the first tracking system and the determined second position of the second tracking system;
   transforming the determined first position with the first tracking system relative to the determined second position with the second tracking system;
   collecting a first set of position data with the first tracking system and a second set of position data with the second tracking system;
   determining a plurality of vectors, wherein one vector is determined between each synchronously related position data in the first set and the second set;
   interpolating position data collected with the first tracking system to register the first coordinate system to the second coordinate system of the second tracking system; and
   translating a determined third position of the first tracking system relative to a selected position of the second tracking system based on the determined vector displacement.

2. The method of claim 1, further comprising:
   determining the determined first position and second position with a single instrument having a first tracking device trackable with a first tracking system and a second tracking device trackable with a second tracking system.

3. The method of claim 2, further comprising:
   determining a physical distance, direction, or both between the first tracking device and the second tracking device relative to each other on the single instrument.

4. The method of claim 3, wherein the selected determined position is a determined position of a single physical location that is determined with both the first tracking system and the second tracking system.

5. The method of claim 2, further comprising:
   determining a plurality of selected determined positions with the single instrument;
   wherein each of the selected determined positions is a position determined with both a first tracking system and a second tracking system by tracking the respective tracking device.

6. The method of claim 5, further comprising:
   determining a transformation of at least a sub-plurality of the plurality of selected determined positions between the first tracking system and the second tracking system.

7. The method of claim 6, further comprising:
   determining an affine transformation as the determined transformation; and
   transforming a first tracking system determined position to a second tracking system determined position.

8. The method of claim 6, further comprising:
   determining the first selected position with the first tracking system;
   wherein translating a first selected position to a second selected position of the second tracking system includes transforming the first selected position with the determined transformation.

9. The method of claim 8, further comprising:
   acquiring image data having an image data coordinate system;
   registering the second coordinate system of the second tracking system to the image data coordinate system of image data; and
   illustrating the first selected position on a display relative to the image data based upon the translation of the first selected position with the determined transformation.

10. The method of claim 9, further comprising:
    displaying the acquired image data; and
    displaying a position of an instrument superimposed on the displayed image data.

11. The method of claim 9, further comprising:
    generating an electromagnetic field relative to an anatomy to define the second coordinate system of the second tracking system;
    positioning axis injection electrodes relative to the anatomy to inject a current between respective pairs of axis electrodes into the anatomy to define the first coordinate system of the first tracking system; and operating the first tracking system and the second tracking system substantially simultaneously to determine the selected determined position with both the first tracking system and the second tracking system.

12. The method of claim 1, wherein the selected determined position includes a first tracking system selected determined position displaced a known distance and orientation from a second tracking system selected determined position.

13. The method of claim 1, further comprising:
determining the determined first position with a first instrument having a first tracking device trackable with the first tracking system and the determined second position with a second instrument having a second tracking device trackable with the second tracking system.

14. The method of claim 13, further comprising:
moving the second instrument through the first instrument;
determining when the second tracking device of the second instrument is aligned with the first tracking device of the first instrument; and
having instructions executed by a processor to determine the registration by determining that the first tracking device and the second tracking device are at the same place within a space when it is determined that the second tracking device of the second instrument is aligned with the first tracking device of the first instrument.

15. The method of claim 13, further comprising:
moving the first instrument to a first known location in a space;
moving the second instrument to a position known relative to the first instrument;
having instructions executed by a processor to determine the registration by determining that the first tracking device and the second tracking device are at the known relative position.

16. The method of claim 15, wherein moving the first instrument to the first known location in the space includes placing a dynamic reference frame in the space;
wherein moving the second instrument to the position known relative to the first instrument includes moving the second instrument to the dynamic reference frame.

17. The method of claim 13, further comprising:
moving the first instrument to a first selected location;
operating a tracking system to track the first tracking device to the first selected location;
identifying the first selected location with an external indication source;
moving the second instrument over the first instrument;
wherein determining the registration of the first coordinate system of the first tracking system and the second coordinate system of the second tracking system occurs when the second tracking device reaches the first selected location identified with the external indication source.

18. The method of claim 13, further comprising:
registering the first coordinate system of the first tracking device to an image coordinate system of an image data.

19. The method of claim 1, further comprising:
synchronizing a timing of the determination of the first position with the first tracking system and the second position with the second tracking system; and
generating a look-up table of the determined vectors.

20. A method of correlating a first coordinate system of a first tracking system and a second coordinate system of a second tracking system, comprising:

synchronously collecting a first registration position data with the first tracking system having a first coordinate system and a second registration position data with the second tracking system having a second coordinate system;
transforming the first registration position data collected with the first tracking system relative to the second registration position data collected with the second tracking system;
collecting a first set of position data with the first tracking system and a second set of position data with the second tracking system;
determining a plurality of vectors, wherein one vector is determined between each synchronously related position data in the first set and the second set;
generating a look-up table of the determined vectors; and
interpolating position data collected with the first tracking system to register the first coordinate system to the second coordinate system of the second tracking system.

21. The method of claim 20, further comprising:
obtaining image data of a patient having an image data coordinate system; and
registering the second coordinate system to the image data coordinate system;
wherein interpolating the position data includes displaying the position data on a display device relative to the image data.

22. The method of claim 21, further comprising:
determining a position of an instrument with only the second tracking system.

23. The method of claim 22, further comprising:
illustrating an icon super-imposed on the obtained image data of the patient based on the determined position of the instrument with the second tracking system and the registration of the second coordinate system to the image data coordinate system and the interpolated position data collected with the first tracking system.

24. The method of claim 21, further comprising:
determining a transformation between the first registration position data and the second registration position data determined with the respective first and second tracking systems.

25. The method of claim 24, wherein determining the transformation includes optimizing an affine transformation including translating the first registration position data to center at an origin, scaling the first registration position data, rotating the first registration position data around a selected axis, and translating the first registration position data from the origin to a center of the second registration position data.

26. The method of claim 25, further comprising:
determining a relative position between a first tracking device trackable with the first tracking system and a second tracking device trackable with the second tracking system;
wherein the first registration position data is determined with the first tracking device and the second registration position data is determined with the second tracking device.

27. The method of claim 26, wherein collecting the first set of position data and collecting the second set of position data is collected respectively with the first tracking device and the second tracking device;
wherein determining the plurality of vectors includes determining a vector based upon a known position of the first tracking device and the second tracking device;
wherein generating the look-up table includes storing the plurality of the vectors in a memory device.

28. The method of claim 27, wherein generating a look-up table includes storing the plurality of vectors in an octree arrangement.

29. The method of claim 28, further comprising:
collecting a map set of position data with the second tracking system;
wherein interpolating position data includes accessing the octree to determine the eight (8) nearest cells of a selected position and interpolating a displacement of the map set of position data points in the map position data;
wherein the interpolation of the map position data determines the position of the map position data relative to the first coordinate system.

30. The method of claim 28, wherein interpolating position data includes interpolating the collected second set of position data to determine an interpolated coordinate of at least a selected sub-plurality of the second set of position data;
wherein the interpolated coordinate is a coordinate of the interpolated second position data point in the first tracking system coordinate system.

31. A method of correlating a first coordinate system of a first tracking system and a second coordinate system of a second tracking system, comprising:
obtaining image data of a patient having an image data coordinate system;
registering the image data coordinate system with the second coordinate system of the second tracking system, wherein the second coordinate system of the second tracking system is substantially Euclidean and generated by an electromagnetic localizer;
synchronously collecting a first position data with the first tracking system and a second position data with the second tracking system;
determining a transformation between the first position data and the second position data;
synchronously collecting a plurality of third position data with the first tracking system and a plurality of fourth position data with the second tracking system;
determining a plurality of vectors between synchronously related third position data and fourth position data;
generating a three-dimensional look-up table of the determined vectors;
collecting fifth position data with the first tracking system; and
interpolating the fifth position data relative to the second coordinate system to relate the fifth position data to the registration of the second coordinate system and the image coordinate system.

32. The method of claim 31, wherein registering the image data coordinate system with the second coordinate system includes locating positions in a patient space with the second tracking system and identifying the same related locations in an image space of the obtained image data;
wherein obtaining a location in patient space includes tracking a second tracking device with the second tracking system.

33. The method of claim 31, further comprising:
synchronizing the collection of the first position data with the second position data and the third position data with the fourth position data by at least one of inputting a signal into the first tracking system and the second tracking system substantially simultaneously, measuring a physical change in a patient with the both the first tracking system and the second tracking system, transmitting a timing signal from one of the first tracking system and the second tracking system to the other of the first tracking system and the second tracking system, or combinations thereof;
wherein synchronously collecting a first position data and a second position data and synchronously collecting a plurality of third position data and plurality of fourth position data includes collecting position data with the first tracking system and the second tracking system substantially simultaneously.

34. The method of claim 33, wherein the first position data and the plurality of third position data are collected with a first tracking device and the second position data and the plurality of fourth position data are collected with a second tracking device;
wherein the first tracking device and the second tracking device are substantially fixed relative to one another on a single instrument.

35. The method of claim 34, further comprising:
determining the fixed relative position of the first tracking device to the second tracking device, the second tracking device to the first tracking device or combinations thereof.

36. The method of claim 31, wherein determining the transformation between the first position data and the second position data includes,
determining a transformation between a plurality of first position data wherein each of the plurality of the first position data is collected synchronously with each of a plurality of second position data;
wherein the transformation of the plurality of first position data to the second position data includes determining a best fit transformation of each of the synchronously related first position data and second position data.

37. The method of claim 36, wherein the synchronously collected plurality of first position data, second position data, third position data, and fourth position data are all used to determine a plurality of vectors between the synchronously related plurality of first position data and third position data with the respective plurality of second position data and fourth position data;
wherein the determined plurality of vectors identifies a distance and orientation between the plurality of first position data and third position data and the respective plurality of second position data and plurality of fourth position data.

38. The method of claim 37, wherein interpolating the fifth position data includes accessing the generated three-dimensional look-up table of the determined vectors, determining a location of the fifth position data, determining the eight (8) nearest cells to the position of the fifth position data in the look-up table, and interpolating the fifth position data to the second coordinate system.

39. The method of claim 38, further comprising:
displaying on a display device the obtained image data; and
super-imposing on the displayed obtained image data a graphical representation of an instrument based on the interpolated position of the fifth position data;
wherein collecting the fifth position data with the first tracking system includes determining the position of the instrument only with a first tracking device tracked with the first tracking system.

* * * * *